United States Patent
Chen et al.

(10) Patent No.: US 11,773,172 B2
(45) Date of Patent: Oct. 3, 2023

(54) ANTI-EGFR ANTIBODY POLYPEPTIDE

(71) Applicant: WUXI BIOLOGICS IRELAND LIMITED, Dublin (IE)

(72) Inventors: Yunying Chen, Shanghai (CN); Jing Li, Shanghai (CN)

(73) Assignee: WUXI BIOLOGICS IRELAND LIMITED, Dublin (IE)

( * ) Notice: Subject to any disclaimer, the term of this patent is extended or adjusted under 35 U.S.C. 154(b) by 267 days.

(21) Appl. No.: 16/981,836

(22) PCT Filed: Mar. 18, 2019

(86) PCT No.: PCT/CN2019/078481
§ 371 (c)(1),
(2) Date: Sep. 17, 2020

(87) PCT Pub. No.: WO2019/179389
PCT Pub. Date: Sep. 26, 2019

(65) Prior Publication Data
US 2021/0115146 A1    Apr. 22, 2021

(30) Foreign Application Priority Data
Mar. 19, 2018  (WO) ............... PCT/CN2018/079487

(51) Int. Cl.
*C07K 16/28* (2006.01)
*G01N 33/74* (2006.01)

(52) U.S. Cl.
CPC ......... *C07K 16/2863* (2013.01); *G01N 33/74* (2013.01); *C07K 2317/565* (2013.01); *C07K 2317/569* (2013.01); *C07K 2317/92* (2013.01); *G01N 2333/71* (2013.01)

(58) Field of Classification Search
None
See application file for complete search history.

(56) References Cited

U.S. PATENT DOCUMENTS

| | | |
|---|---|---|
| 2009/0252681 A1 | 10/2009 | Laeremans et al. |
| 2017/0128592 A1 | 5/2017 | Poojari et al. |

FOREIGN PATENT DOCUMENTS

| | | |
|---|---|---|
| AU | 2014203036 A1 | 7/2014 |
| CN | 105940113 A | 9/2016 |
| CN | 107367611 A | 11/2017 |
| WO | 2004041867 A2 | 5/2004 |
| WO | 2005044858 A1 | 5/2005 |
| WO | 2007066106 A1 | 6/2007 |
| WO | 2015/073721 A1 | 5/2015 |
| WO | 2017125831 A1 | 7/2017 |
| WO | 2017/153402 A1 | 9/2017 |
| WO | 2017153402 A1 | 9/2017 |
| WO | WO 2019/179390 | * 9/2019 |

OTHER PUBLICATIONS

Ahdi Khosroshahi Shiva et al: "Development and evaluation of a single domain antibody against human epidermal growth factor receptor (EGFR)", Protein Expression and Purification, Academic Press, San Diego, CA XP029393685.

Rob C Roovers et al: "Efficient inhibition of EGFR signalling and of tumour growth by antagonistic anti-EGFR Nanobodies", Cancer Immunology, Immunotherapy, Springer, Berlin, DE, vol. 56, No. 3, May 30, 2006 (May 30, 2006), pp. 303-317, XP019472685, ISSN: 1432-0851, DOI: 10.1007/S00262-006-0180-4.

Fumiyoshi Okazaki et al: "Efficient heterologous expression and secretion inof a llama variable heavy-chain antibody fragment Vagainst EGFR", Appl Microbiol Biotechnol. Oct. 2012;96(1):81-8. doi: 10.1007/s00253-012-4158-1. Epub May 29, 2012.

Kobra Omidfar et al: "Single Domain Antibodies: A New Concept for Epidermal Growth Factor Receptor and EGFRVIII Targeting", DNA and Cell Biology XP055731323.

Kendrick B. Turner et al: "Improving the targeting of therapeutics with single-domain antibodies", Expert Opinion On Drug Delivery XP055731285.

International Search Report for International Application No. PCT/CN2019/078481, dated Jun. 24, 2019, 4 pages.

* cited by examiner

*Primary Examiner* — Marianne P Allen
(74) *Attorney, Agent, or Firm* — PROCOPIO, CORY, HARGREAVES & SAVITCH LLP

(57) ABSTRACT

The present disclosure provides anti-EGFR antibody polypeptides, polynucleotides encoding the same, pharmaceutical compositions comprising the same, and the uses thereof.

7 Claims, 11 Drawing Sheets
Specification includes a Sequence Listing.

| Abs | A431 | |
|---|---|---|
| | IC$_{50}$ (nM) | Max Inhibition % |
| Erbitux | 6.1 | 96.2 |
| W5626-2C2-z22 | 22.6 | 80.9 |
| W5626-2C10-z5 | 10.4 | 98.9 |
| Isotype | NA | 9.6 |

| Abs | A431 | | |
|---|---|---|---|
| | $EC_{50}$ (nM) | Min Viability % | Min Viability % Exclude 10 nM |
| Erbitux | 0.10 | 3.8 | 7.1 |
| W5626-2C2-z22 | 0.17 | 5.4 | 11.8 |
| W5626-2C10-z5 | 0.21 | 5.4 | 11.4 |
| Isotype | 1.98 | 28.7 | 58.7 |
| Fab-ZAP Only | 2.70 | 26.2 | 66.5 |

```
                         SEQUENCE LISTING

<160> NUMBER OF SEQ ID NOS: 14

<210> SEQ ID NO 1
<211> LENGTH: 10
<212> TYPE: PRT
<213> ORGANISM: Lama glama

<400> SEQUENCE: 1

Gly Arg Thr Phe Ser Ser Tyr Ala Met Gly
1               5                   10

<210> SEQ ID NO 2
<211> LENGTH: 17
<212> TYPE: PRT
<213> ORGANISM: Lama glama

<400> SEQUENCE: 2

Ala Asp Arg Trp Ser Gly Gly Asn Thr Arg Tyr Ala Asp Ser Val Lys
1               5                   10                  15
Gly

<210> SEQ ID NO 3
<211> LENGTH: 20
<212> TYPE: PRT
<213> ORGANISM: Lama glama

<400> SEQUENCE: 3

Thr Tyr Leu Ser Ser Asp Tyr Glu Trp Gly Val Pro Pro Lys Ala Tyr
1               5                   10                  15
Asp Tyr Asp Tyr
            20

<210> SEQ ID NO 4
<211> LENGTH: 10
<212> TYPE: PRT
<213> ORGANISM: Lama glama

<400> SEQUENCE: 4
```

```
Gly Arg Thr His Ser Asn Tyr Val Met Gly
1               5                  10
```

<210> SEQ ID NO 5
<211> LENGTH: 17
<212> TYPE: PRT
<213> ORGANISM: Lama glama

<400> SEQUENCE: 5

```
Gly Ile Ser Arg Thr Tyr Gly Asn Thr Tyr Tyr Arg Asp Ser Val Glu
1               5                  10                  15

Gly
```

<210> SEQ ID NO 6
<211> LENGTH: 17
<212> TYPE: PRT
<213> ORGANISM: Lama glama

<400> SEQUENCE: 6

```
Asp Pro Thr Arg Ser Glu Val Ile Leu Thr Thr Ser His Arg Tyr Val
1               5                  10                  15

Tyr
```

<210> SEQ ID NO 7
<211> LENGTH: 129
<212> TYPE: PRT
<213> ORGANISM: Lama glama

<400> SEQUENCE: 7

```
Ala Val Gln Leu Val Glu Ser Gly Gly Gly Leu Val Gln Ala Gly Gly
1               5                  10                  15

Ser Leu Thr Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Asp Arg Trp Ser Gly Gly Asn Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Tyr Leu Ser Ser Asp Tyr Glu Trp Gly Val Pro Pro Lys
            100                 105                 110

Ala Tyr Asp Tyr Asp Tyr Trp Gly Gln Gly Thr Gln Val Thr Val Ser
        115                 120                 125

Ser
```

<210> SEQ ID NO 8
<211> LENGTH: 387
<212> TYPE: DNA
<213> ORGANISM: Lama glama

<400> SEQUENCE: 8

```
gcggtacaac tggtggagtc tgggggaggt ctggtgcagg ctggggttc tctgacgctc      60 tcctgtgcag cctctggacg caccttcagt agctatgcca tgggctggtt ccgccaggct    120
ccagggaagg agcgtgagtt tgtagcagct gataggtgga gtggtggtaa cacacgctat    180
gcagactccg tgaagggccg attcaccatc tccagagaca acgccaagaa cacggtgtat    240
```

```
ctgcaaatga acagcctgaa acctgaggac acggccgttt attactgtgc agccacatat    300
ttgagtagcg actatgagtg gggggtccct ccgaaggcct atgactatga ctactggggc    360
caggggaccc aggtcaccgt ctcctca                                        387
```

```
<210> SEQ ID NO 9
<211> LENGTH: 129
<212> TYPE: PRT
<213> ORGANISM: Artificial Sequence
<220> FEATURE:
<223> OTHER INFORMATION: Synthetic

<400> SEQUENCE: 9
```

Ala Val Gln Leu Val Glu Ser Gly Gly Gly Leu Val Gln Pro Gly Gly
1               5                   10                  15

Ser Leu Thr Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Asp Arg Trp Ser Gly Gly Asn Thr Arg Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Thr Tyr Leu Ser Ser Asp Tyr Glu Trp Gly Val Pro Pro Lys
            100                 105                 110

Ala Tyr Asp Tyr Asp Tyr Trp Gly Gln Gly Thr Leu Val Thr Val Ser
        115                 120                 125

Ser

```
<210> SEQ ID NO 10
<211> LENGTH: 387
<212> TYPE: DNA
<213> ORGANISM: Artificial Sequence
<220> FEATURE:
<223> OTHER INFORMATION: Synthetic

<400> SEQUENCE: 10
gccgtgcagc tggtggagag cggaggagga ctggtgcagc ctggcggaag cctgaccctg    60
tcctgcgctg ccagcggcag gaccttcagc agctacgcca tgggctggtt caggcaggct    120
cctggcaagg agagggagtt tgtggccgcc gacagatgga gcggcggcaa taccagatac    180
gccgacagcg tgaagggcag gttcaccatc agcagggata acgccaagaa taccctgtac    240
ctgcagatga actccctgag ggccgaggac accgccgtgt actactgcgc cgccacctac    300
ctgagcagcg attacgagtg gggcgtgccc cccaaggcct atgactacga ctactggggc    360
cagggcacac tggtgaccgt gagcagc                                        387
```

```
<210> SEQ ID NO 11
<211> LENGTH: 126
<212> TYPE: PRT
<213> ORGANISM: Lama glama

<400> SEQUENCE: 11
```

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr His Ser Asn Tyr
            20                  25                  30

Val Met Gly Trp Phe Arg Gln Ala Pro Gly Gln Glu Arg Glu Phe Val
         35                  40                  45

Ala Gly Ile Ser Arg Thr Tyr Gly Asn Thr Tyr Tyr Arg Asp Ser Val
 50                  55                  60

Glu Gly Arg Phe Thr Ile Ser Val Asp Asn Pro Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Asp Pro Thr Arg Ser Glu Val Ile Leu Thr Thr Ser His Arg
             100                 105                 110

Tyr Val Tyr Trp Gly Gln Gly Thr Leu Val Thr Val Ser Ser
         115                 120                 125

<210> SEQ ID NO 12
<211> LENGTH: 378
<212> TYPE: DNA
<213> ORGANISM: Lama glama

<400> SEQUENCE: 12
gaggtgcagt tggtggagtc tgggggagga ttggtgcagg ctggggactc tctgagactc      60
tcctgtgcag cctccggacg cacccacagt aactatgtca tgggctggtt ccgccaggct     120
ccagggcagg agcgtgagtt tgtagcaggt attagcagga cttatggtaa tacatactat     180
agagactccg tggagggccg attcaccatc tccgtagaca accccaagaa cacggtgtat     240
ttgcaaatga acagcctgaa acctgaggac acggccgttt attactgtgc agcagacccg     300
acccgttctg aagtgatact tactacttca caccgctatg tctactgggg ccaggggacc     360
ctggtcactg tctcctca                                                    378

<210> SEQ ID NO 13
<211> LENGTH: 126
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr His Ser Asn Tyr
             20                  25                  30

Val Met Gly Trp Phe Arg Gln Ala Pro Gly Gln Glu Arg Glu Phe Val
         35                  40                  45

Ala Gly Ile Ser Arg Thr Tyr Gly Asn Thr Tyr Tyr Arg Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Asp Pro Thr Arg Ser Glu Val Ile Leu Thr Thr Ser His Arg
             100                 105                 110

Tyr Val Tyr Trp Gly Gln Gly Thr Leu Val Thr Val Ser Ser
         115                 120                 125

<210> SEQ ID NO 14
<211> LENGTH: 378
<212> TYPE: DNA

<213> ORGANISM: Artificial Sequence
<220> FEATURE:
<223> OTHER INFORMATION: Synthetic

<400> SEQUENCE: 14

```
gaggtgcagc tggtggagtc cggaggagga ctggtgcagc ccggaggatc tttaagactg      60
agctgcgccg ccagcggcag aacccacagc aactacgtga tgggctggtt ccgtcaagct     120
cccggtcaag agagggagtt cgtggccggc atcagcagga cctacggcaa cacctactac     180
agggacagcg tggagggtcg tttcaccatc tctcgtgaca acagcaagaa cactttatat     240
ttacagatga actctttaag ggccgaggac accgccgtgt actactgcgc cgctgatccc     300
actcgtagcg aggtgatttt aaccacaagc catcgttacg tgtactgggg acaaggtact     360
ttagtgaccg tgtccagc                                                   378
```

ANTI-EGFR ANTIBODY POLYPEPTIDE

CROSS REFERENCE TO RELATED APPLICATION

The present application is a U.S. National Stage entry of PCT Application No: PCT/CN2019/078481 filed on Mar. 18, 2019 which claims the priority to PCT Application Number PCT/CN2018/079487, filed on Mar. 19, 2018.

FIELD OF THE INVENTION

The present disclosure generally relates to novel anti-human EGFR antibody polypeptide.

BACKGROUND

EGFR belongs to ERBB receptor tyrosine kinase superfamily. Binding of EGF to EGFR leads to tyrosine phosphorylation and receptor dimerization with other family members resulting in enhanced uncontrolled proliferation. EGFR is overexpressed in several types of cancer, where EGFR and its family members are the major contributors of a complex signaling cascade that modulates growth, signaling, differentiation, adhesion, migration and survival of cancer cells. Therefore EGFR and its family members have emerged as attractive candidates for anti-cancer therapy.

Two EGFR-targeted antibodies, cetuximab (Erbitux) and panitumumab (Vectibix), have been approved by the US Food and Drug Administration for the treatment of several solid cancer, including colorectal, head and neck cancer, NSCLC, pancreatic cancer. These antibodies block the binding of ligands to EGFR and downstream signals, therefore mediate antitumor immune responses. These antibodies also induce the internalization and degradation of EGFR, thereby leading to signal termination.

A single-domain antibody (sdAb) is an antibody consisting of a single monomeric variable antibody domain. Like a whole antibody, it is able to bind selectively to a specific antigen. Single-domain antibodies are much smaller than common antibodies which are composed of two heavy protein chains and two light chains. The first single-domain antibodies were engineered from heavy-chain antibodies found in camelids (Hamers-Casterman C, Atarhouch T, Muyldermans S, Robinson G, Hamers C, Songa E B, Bendahman N, Hamers R (1993) Naturally occurring antibodies devoid of light chains. Nature 363(6428):446-448); these are called VHH fragments. Currently, most research into single-domain antibodies is based on heavy chain variable domains.

Single-domain antibodies have many advantages. For instance, they generally display high solubility and stability and can also be readily produced in yeast, plant, and mammalian cells (Harmsen M M, De Haard H J (2007) Properties, production, and applications of camelid single-domain antibody fragments. Appl Microbiol Biotechnol 77(1):13-22). Further, they have good thermal stability and good tissue penetration. And they are also cost efficient in production. The advantages of single-domain antibodies make them suitable for various biotechnological and therapeutic applications. For instance, they are useful in the treatment of diseases, including but not limited to cancer, infectious, inflammatory and neurodegenerative diseases.

Although antibodies against EGFR are been developed, there are still spaces for improvement for antibody against EGFR as a therapeutic agent. Accordingly, there is desire in the art to develop novel anti-EGFR antibodies, particularly single-domain antibodies against EGFR.

BRIEF SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides novel monoclonal anti-EGFR antibodies, amino acid and nucleotide sequences thereof, and uses thereof.

In one aspect the present disclosure provides an antibody polypeptide comprising a heavy chain variable domain that specifically binds to EGFR (e.g. human EGFR), wherein the heavy chain variable domain comprises:

1, 2, or 3 heavy chain complementarity determining region (CDR) sequences selected from the group consisting of: SEQ ID NO: 1, SEQ ID NO: 2, SEQ ID NO: 3, SEQ ID NO: 4, SEQ ID NO: 5 and SEQ ID NO: 6.

In certain embodiments, the heavy chain variable domain comprises a heavy chain variable region selected from the group consisting of:

a) a heavy chain variable region comprising 1, 2, or 3 CDR sequences selected from SEQ ID NO: 1, SEQ ID NO: 2 and SEQ ID NO: 3; and b) a heavy chain variable region comprising 1, 2, or 3 CDR sequences selected from SEQ ID NO: 4, SEQ ID NO: 5 and SEQ ID NO: 6.

In certain embodiments, the heavy chain variable domain comprises a heavy chain variable region selected from the group consisting of SEQ ID NO: 7, SEQ ID NO: 9, SEQ ID NO: 11 and SEQ ID NO: 13, and a homologous sequence thereof having at least 80% sequence identity yet retaining specific binding affinity to EGFR.

In certain embodiments, the antibody polypeptide as provided herein further comprises one or more amino acid residue substitutions or modifications yet retaining specific binding affinity to EGFR.

In certain embodiments, at least one of the substitutions or modifications is in one or more of the CDR sequences, and/or in one or more of the VH sequences but not in any of the CDR sequences.

In certain embodiments, the antibody polypeptide is a single domain antibody or a heavy-chain antibody.

In certain embodiments, the heavy chain variable domain is derived from a VHH domain.

In certain embodiments, the antibody polypeptide further comprises an immunoglobulin constant region, optionally a constant region of human Ig, or optionally a constant region of human IgG.

In certain embodiments, the antibody polypeptide is isolated.

In certain embodiments, the heavy chain variable domain is of camelid origin or is humanized.

In certain embodiments, the antibody polypeptide is a nanobody.

In certain embodiments, the antibody polypeptide as provided herein is capable of specifically binding to human EGFR at an $EC_{50}$ value of no more than 1 nM as measured by flow cytometry.

In certain embodiments, the antibody polypeptide as provided herein is capable of specifically binding to human EGFRvIII at an $EC_{50}$ value of no more than 2.5 nM as measured by flow cytometry.

In certain embodiments, the antibody polypeptide as provided herein is capable of specifically binding to Cynomolgus monkey EGFR, and/or mouse EGFR.

In certain embodiments, the antibody polypeptide as provided herein is linked to one or more conjugate moieties.

In certain embodiments, the conjugate moiety comprises a clearance-modifying agent, a chemotherapeutic agent, a toxin, a radioactive isotope, a lanthanide, a luminescent label, a fluorescent label, an enzyme-substrate label, a DNA-alkylators, a topoisomerase inhibitor, a tubulin-binders, or other anticancer drugs.

In another aspect, the present disclosure provides an antibody or an antigen-binding fragment thereof, which competes for the same epitope with the antibody polypeptide of any of the preceding claims.

The present disclosure also provides a pharmaceutical composition comprising the antibody polypeptide as provided herein, the antibody or an antigen-binding fragment thereof as provided herein, and a pharmaceutically acceptable carrier.

The present disclosure also provides a polynucleotide encoding the antibody polypeptide as provided herein.

In certain embodiments, the polynucleotide as provided herein comprises a nucleotide sequence selecting from a group consisting of SEQ ID NO: 8, SEQ ID NO: 10, SEQ ID NO: 12 and SEQ ID NO: 14, and/or a homologous sequence thereof having at least 80% sequence identity, and/or a variant thereof having only degenerate substitutions.

The present disclosure also provides a vector comprising the polynucleotide as provided herein.

The present disclosure also provides a host cell comprising the vector as provided herein.

The present disclosure also provides a method of expressing the antibody polypeptide as provided herein, comprising culturing the host cell as provided herein under the condition at which the vector as provided herein is expressed.

The present disclosure also provides a method of treating a disease or condition in a subject that would benefit from modulation of EGFR activity, comprising administering to the subject a therapeutically effective amount of the antibody polypeptide as provided herein or the pharmaceutical composition as provided herein.

In certain embodiments, the disease or condition is an EGFR related disease or condition.

In certain embodiments, the disease or condition is cancer or inflammatory disease.

In certain embodiments, the cancer is colorectal cancer, skin cancer, head and neck cancer, non-small cell lung cancer, gastrointestinal cancer, glioblastoma, melanoma, breast cancer, cervical cancer, ovarian cancer, endometrial cancer, prostate cancer, renal cancer, bladder cancer, esophageal cancer, brain cancer, liver cancer, pancreatic cancer, hepatocellular cancer, or squamous cell carcinoma, and wherein the inflammatory disease is Alzheimer's disease, asthma, atopic allergy, allergy, atherosclerosis, bronchial asthma, eczema, glomerulonephritis, graft vs. host disease, hemolytic anemias, osteoarthritis, psoriasis, sepsis, stroke, transplantation of tissue and organs, vasculitis, diabetic retinopathy or ventilator induced lung injury.

In certain embodiments, the subject is human.

In certain embodiments, the administration is via oral, nasal, intravenous, subcutaneous, sublingual, or intramuscular administration.

In another aspect, the present disclosure provides a method of modulating EGFR activity in an EGFR-expressing cell, comprising exposing the EGFR-expressing cell to the antibody polypeptide as provided herein.

The present disclosure also provides a method of detecting presence or amount of EGFR in a sample, comprising contacting the sample with the antibody polypeptide as provided herein, and determining the presence or the amount of EGFR in the sample.

The present disclosure also provides a method of diagnosing a EGFR related disease or condition in a subject, comprising: a) contacting a sample obtained from the subject with the antibody polypeptide as provided herein; b) determining presence or amount of EGFR in the sample; and c) correlating the presence or the amount of EGFR to existence or status of the EGFR related disease or condition in the subject.

The present disclosure also provides use of the antibody polypeptide as provided herein in the manufacture of a medicament for treating an EGFR related disease or condition in a subject.

The present disclosure also provides use of the antibody polypeptide as provided herein in the manufacture of a diagnostic reagent for diagnosing an EGFR related disease or condition.

The present disclosure also provides a kit comprising the antibody polypeptide as provided herein, useful in detecting EGFR.

DETAILED DESCRIPTION OF THE INVENTION

Figure 1A:
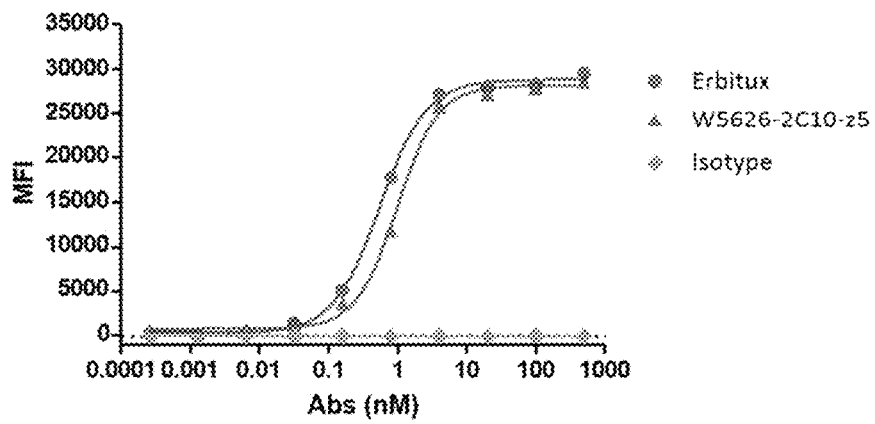
FIG. 1A shows that W5626-2C10-z5 and W5626-2C2-z22 bind to human EGFR with an $EC_{50}$ (0.99 nM and 0.83 nM) similar to Erbitux as measured by FACS.
Figure 1A:
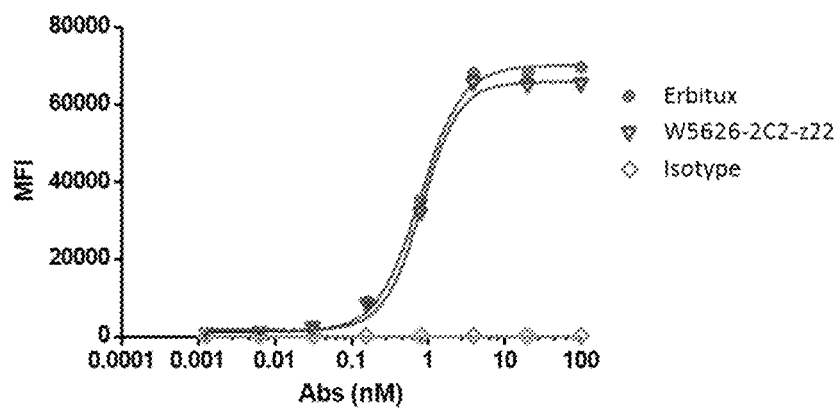
Figure 1B:
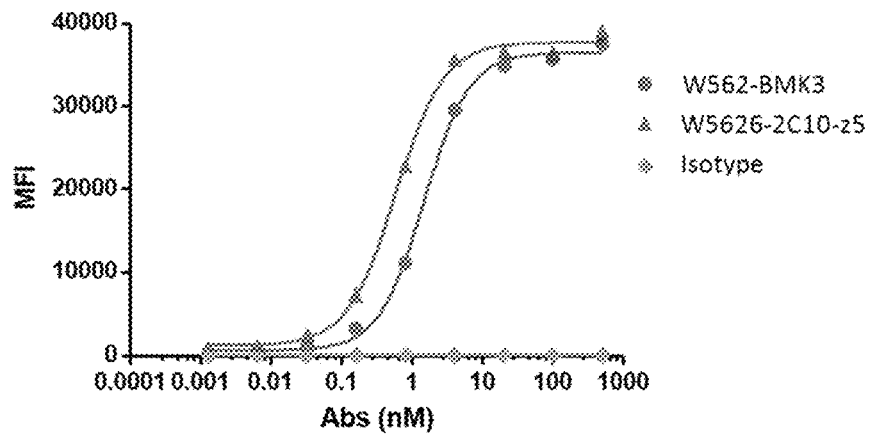
FIG. 1B shows that W5626-2C10-z5 and W5626-2C2-z22 bind to monkey EGFR with an $EC_{50}$ (0.58 nM and 0.25 nM, respectively) better than W562-BMK3 as measured by FACS.
Figure 1B:
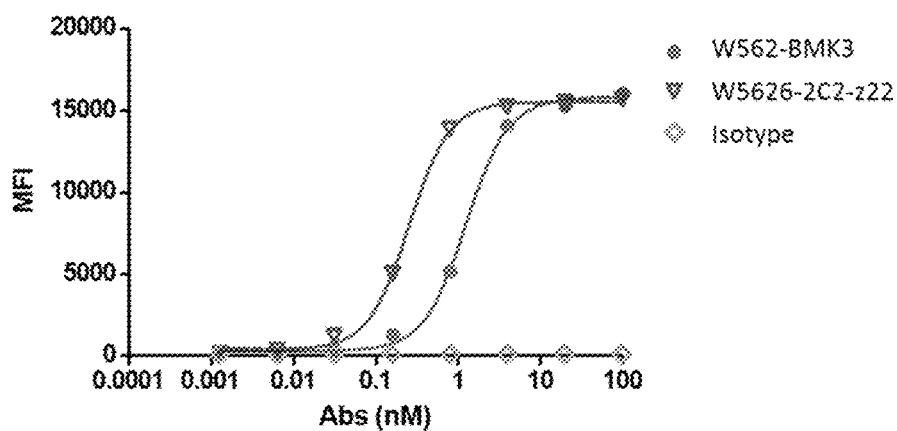
Figure 1C:
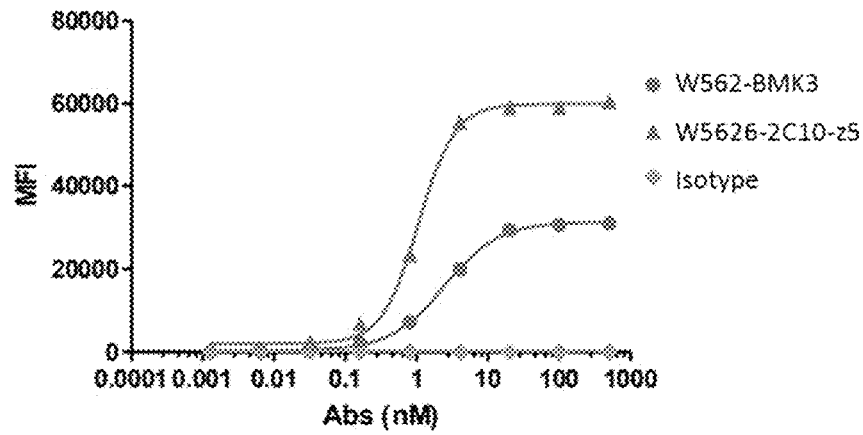
FIG. 1C shows that W5626-2C10-z5 and W5626-2C2-z22 bind to mouse EGFR with an $EC_{50}$ (1.06 nM and 0.65 nM, respectively) better than W562-BMK3 as measured by FACS.
Figure 1C:
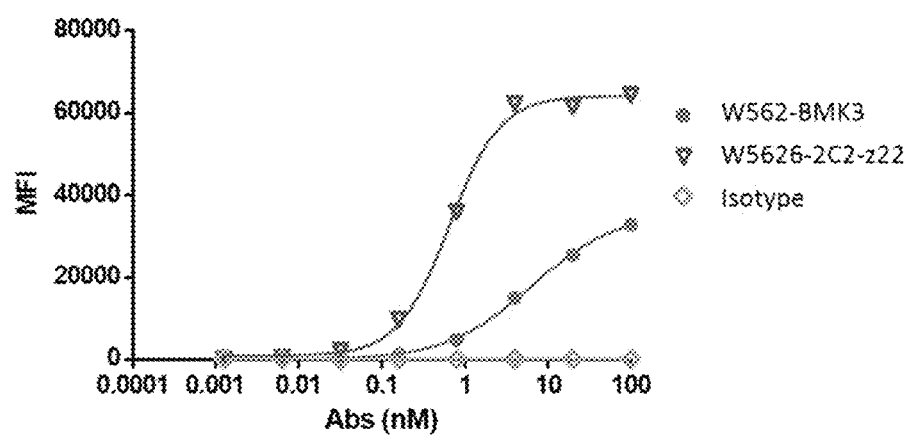

The following description of the disclosure is merely intended to illustrate various embodiments of the disclosure.

As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, or monovalent antibody that binds to a specific antigen. The term "antibody" as used herein intends to encompass broadly to both conventional four-chain antibodies and also less-conventional antibodies that do not have four chains (such as antibodies naturally devoid of light chains).

A conventional intact antibody comprises two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as λ or κ, while each light chain consists of a variable region ($V_L$) and a constant region. The conventional antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., Sequences of Proteins of Immunological Interest, 5$^{th}$ Ed. Public Health Service, National Institutes of Health, Bethesda, Md. (1991); Marie-Paule Lefranc et al, Developmental and Comparative Immunology, 27: 55-77 (2003); Marie-Paule Lefranc et al, Immunome Research, 1(3), (2005); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

Unlike conventional antibodies which are heterotetramers, there are homodimeric immunoglobulins and are naturally devoid of light chains. Such antibodies are found in, for example, camelids (camel, dromedary, llama, alpaca, etc.), and are also called heavy-chain antibodies with a molecular weight of about 80 kD (Hamers-Casterman C. et al., 1993, Nature, 363:446-448).

The term "antibody polypeptide" as used herein refers to an antigen-binding protein or polypeptide comprising an antibody fragment (such as a CDR, and/or a variable region sequence). An antibody polypeptide can be, for example, a heavy-chain antibody (a VHH antibody), a variable domain of a heavy-chain antibody, a VHH domain, or a single domain antibody containing a single variable domain. The antibody polypeptide may further comprise additional domains such as a constant region, an Fc domain, and/or a second variable domain specifically binding to a different antigen or different epitope.

"Heavy-chain antibody" and "VHH antibody" are interchangeably used herein, and refers to an antibody that contains two $V_H$ domains and no light chains (Riechmann L. and Muyldermans S., J Immunol Methods. December 10; 231(1-2):25-38 (1999); Muyldermans S., J Biotechnol. June; 74(4):277-302 (2001); WO94/04678; WO94/25591; U.S. Pat. No. 6,005,079). Although devoid of light chains, heavy-chain antibodies have an authentic antigen-binding repertoire (Hamers-Casterman C. et al., 1993, Nature, 363:446-448; Nguyen V K. et al., 2002, Immunogenetics, 54(1):39-47; Nguyen V K. et al., 2003, Immunology, 109(1): 93-101).

"VHH domain" as used herein refers to the heavy chain variable domain of a heavy chain antibody. VHH domain represents the smallest known antigen-binding unit generated by adaptive immune responses (Koch-Nolte F. et al., 2007, FASEB J., 21(13):3490-8. Epub 2007 Jun. 15).

A "single domain antibody" refers to an antibody fragment containing only a single variable region of a heavy chain or a single variable region of a light chain. In certain embodiments, the single domain antibody has or consists of only a single heavy-chain variable domain of a heavy-chain antibody.

A "nanobody" refers to an antibody fragment that consists of a VHH domain from a heavy chain antibody and two constant domains, CH2 and CH3.

In certain instances, two or more VHH domains can be covalently joined with a peptide linker to create a bivalent or multivalent domain antibody. The two VHH domains of a bivalent domain antibody may target the same or different antigens.

The term "bivalent" as used herein refers to an antibody or antibody polypeptide having two antigen-binding sites; the term "monovalent" refers to an antibody or antibody polypeptide having only one single antigen-binding site; and the term "multivalent" refers to an antibody or antibody polypeptide having multiple antigen-binding sites. In some embodiments, the antibody or antibody polypeptide is bivalent.

The term "chimeric" as used herein, means an antibody or antibody polypeptide having a portion of heavy chain derived from one species, and the rest of the heavy chain derived from a different species. In an illustrative example, a chimeric antibody may comprise a constant region derived from human and a variable region from a non-human animal, such as from camelidae. In some embodiments, the non-human animal is a mammal, for example, a camelidae, a mouse, a rat, a rabbit, a goat, a sheep, a guinea pig, or a hamster.

The term "humanized" as used herein means that the antibody or antibody polypeptide comprises CDRs derived from non-human animals, FR regions derived from human, and when applicable, the constant regions derived from human.

"EGFR" as used herein, can be derived from any vertebrate source, including mammals such as primates (e.g. humans, monkeys) and rodents (e.g., mice and rats). Exemplary sequence of human EGFR includes human EGFR protein (Genbank accession No.: GI: 110002567 and GI: 63101670). Exemplary sequence of EGFR includes *Macaca fascicularis* (monkey) EGFR protein (Genbank accession No.: GI: 544419950, GI: 544419948, GI: 544419952); *Mus musculus* (mouse) EGFR protein Genbank accession No.: GI: 10880776 and GI: 5524153); *Rattus norvegicus* (Rat) EGFR protein (Genbank accession No.: GI: 315227975, GI: 315227973, GI: 6478868).

The term "EGFR" as used herein is intended to encompass any form of EGFR, for example, 1) native unprocessed EGFR molecule, "full-length" EGFR chain or naturally occurring variants of EGFR, including, for example, splice variants or allelic variants; 2) any form of EGFR that results from processing in the cell; or 3) full length, a fragment (e.g., a truncated form, an extracellular/transmembrane domain) or a modified form (e.g. a mutated form, a glycosylated/PEGylated, a His-tag/immunofluorescence fused form) of EGFR subunit generated through recombinant method.

The term "anti-EGFR" antibody polypeptide refers to an antibody polypeptide that is capable of specific binding EGFR (e.g. human or monkey or mouse or rat EGFR).

The term "specific binding" or "specifically binds" as used herein refers to a non-random binding reaction between two molecules, such as for example between an antibody and an antigen. In certain embodiments, the antibody polypeptides provided herein specifically bind to human EGFR with a binding affinity ($K_D$) of $\leq 10^{-6}$ M (e.g., $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 4 \times 10^{9}$ M, $\leq 3 \times 10^{-9}$ M, $2 \times 10^{-9}$ M, or $\leq 10^{-9}$ M). $K_D$ used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the $K_D$ value can be appropriately determined by using flow cytometry.

The ability to "block binding" or "compete for the same epitope" as used herein refers to the ability of an antibody polypeptide to inhibit the binding interaction between two molecules (e.g. human EGFR and an anti-EGFR antibody) to any detectable degree. In certain embodiments, an antibody polypeptide that blocks binding between two molecules inhibits the binding interaction between the two molecules by at least 85%, or at least 90%. In certain embodiments, this inhibition may be greater than 85%, or greater than 90%.

The term "epitope" as used herein refers to the specific group of atoms or amino acids on an antigen to which an antibody binds. Two antibodies may bind the same or a closely related epitope within an antigen if they exhibit competitive binding for the antigen. For example, if an antibody polypeptide blocks binding of a reference antibody to the antigen by at least 85%, or at least 90%, or at least 95%, then the antibody polypeptide may be considered to bind the same/closely related epitope as the reference antibody.

Those skilled in the art will recognize that it is possible to determine, without undue experimentation, if a given antibody binds to the same epitope as the antibody of present disclosure (e.g., camelid antibody W5626-2C10, W5626-2C2, and humanized antibody W5626-2C10-z5 and W5626-2C2-z22) by ascertaining whether the former prevents the latter from binding to an EGFR antigen polypeptide. If the given antibody competes with the antibody of present disclosure, as shown by a decrease in binding by the antibody of present disclosure to the EGFR antigen polypeptide, then the two antibodies bind to the same, or a closely related, epitope. Or if the binding of a given antibody to the EGFR antigen polypeptide was inhibited by the antibody of present disclosure, then the two antibodies bind to the same, or a closely related, epitope.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "homolog" and "homologous" as used herein are interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1 q on the C1 complex; antibody-dependent cellmediated cytotoxicity (ADCC) induced by binding of Fc region of an antibody to Fc receptor on an effector cell; and phagocytosis.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody polypeptide" refers to the antibody polypeptide having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the antibody polypeptide, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

An "EGFR-related" disease or condition as used herein refers to any disease or condition caused by, exacerbated by, or otherwise linked to increased or decreased expression or activities of EGFR. In some embodiments, the EGFR related condition is cancer and inflammatory disease.

"Cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells. Examples of cancer or tumors include hematological malignancies, oral carcinomas (for example of the lip, tongue or pharynx), digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In certain embodiments, the cancer is selected from ovarian cancer, breast cancer, head and neck cancer, renal cancer, bladder cancer, hepatocellular cancer, and colorectal cancer. In certain embodiments, the cancer is selected from a lymphoma, Hodgkin's lymphoma, non-Hodgkin's lymphoma and B-cell lymphoma.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-EGFR Antibody Polypeptide

The present disclosure provides anti-EGFR antibody polypeptides comprising one or more (e.g. 1, 2, or 3) CDR sequences of an anti-EGFR VHH antibody W5626-2C10, or W5626-2C2.

"W5626-2C10" as used herein refers to a VHH antibody having a heavy chain variable region comprising the sequence of SEQ ID NO: 7.

"W5626-2C10-z5" as used herein refers to a humanized VHH antibody based on W5626-2C10 that comprises a heavy chain variable region comprising the sequence of SEQ ID NO: 9. W5626-2C10-z5 has at least comparable affinity to the antigen as compared with its parent antibody W5626-2C10.

"W5626-2C2" as used herein refers to a VHH antibody having a heavy chain variable region comprising the sequence of SEQ ID NO: 11.

"W5626-2C2-z22" as used herein refers to a humanized VHH antibody based on W5626-2C2 that comprises a heavy chain variable region comprising the sequence of SEQ ID NO: 13. W5626-2C2-z22 has at least comparable affinity to the antigen as compared with its parent antibody W5626-2C2.

Table 1 shows the CDR sequences of these 4 anti-EGFR single domain antibodies. The heavy chain variable region sequences are also provided below in Table 2 and Table 3.

TABLE 1

CDR amino acid sequences

| | | CDR1 | CDR2 | CDR3 |
|---|---|---|---|---|
| W5626-2C10 and W5626-2C10-z5 | HCDR | SEQ ID NO: 1 GRTFSSYAMG | SEQ ID NO: 2 ADRWSGGNTRYADSVKG | SEQ ID NO: 3 TYLSSDYEWGVPPKAYDYDY |
| W5626-2C2 and W5626-2C2-z22 | HCDR | SEQ ID NO: 4 GRTHSNYVMG | SEQ ID NO: 5 GISRTYGNTYYRDSVEG | SEQ ID NO: 6 DPTRSEVILTTSHRYVY |

TABLE 2

Variable region amino acid sequences

| | VH |
|---|---|
| W5626-2C10 | SEQ ID NO: 7 AVQLVESGGGLVQAGGSLTLSCAASGRTFSSYAMGWFRQA PGKEREFVAADRWSGGNTRYADSVKGRFTISRDNAKNTVY LQMNSLKPEDTAVYYCAATYLSSDYEWGVPPKAYDYDYWG QGTQVTVSS |
| W5626-2C10-z5 | SEQ ID NO: 9 AVQLVESGGGLVQPGGSLTLSCAASGRTFSSYAMGWFRQA PGKEREFVAADRWSGGNTRYADSVKGRFTISRDNAKNTLY LQMNSLRAEDTAVYYCAATYLSSDYEWGVPPKAYDYDYWG QGTLVTVSS |
| W5626-2C2 | SEQ ID NO: 11 EVQLVESGGGLVQAGDSLRLSCAASGRTHSNYVMGWFRQA PGQEREFVAGISRTYGNTYYRDSVEGRFTISVDNPKNTVY LQMNSLKPEDTAVYYCAADPTRSEVILTTSHRYVYWGQGT LVTVSS |
| W5626-2C2-z22 | SEQ ID NO: 13 EVQLVESGGGLVQPGGSLRLSCAASGRTHSNYVMGWFRQA PGQEREFVAGISRTYGNTYYRDSVEGRFTISRDNSKNTLY LQMNSLRAEDTAVYYCAADPTRSEVILTTSHRYVYWGQGT LVTVSS |

TABLE 3

Variable region nucleotide sequences

| | VHnu |
|---|---|
| W5626-2C10 | SEQ ID NO: 8 gcggtacaactggtggagtctggggggaggtctggtgcaggc tgggggttctctgacgctctcctgtgcagcctctggacgca ccttcagtagctatgccatgggctggttccgccaggctcca gggaaggagcgtgagtttgtagcagctgataggtggagtgg tggtaacacacgctatgcagactccgtgaagggccgattca ccatctccagagacaacgccaagaacacggtgtatctgcaa atgaacagcctgaaacctgaggacacggccgtttattactg tgcagccacatatttgagtagcgactatgagtgggggtcc ctccgaaggcctatgactatgactactggggccaggggacc caggtcaccgtctcctca |
| W5626-2C10-z5 | SEQ ID NO: 10 gccgtgcagctggtggagagcggaggaggactggtgcagcc tggcggaagcctgaccctgtcctgcgctgccagcggcagga ccttcagcagctacgccatgggctggttcaggcaggctcct ggcaaggagaggagtttgtggccgccgacagatggagcgg cggcaataccagatacgccgacagcgtgaagggcaggttca ccatcagcagggataacgccaagaataccctgtacctgcag atgaactccctgaggggccgaggacaccgccgtgtactactg cgccgccacctacctgagcagcgattacgagtggggggcgtgc ccccaaggcctatgactacgactactggggccagggcaca ctggtgaccgtgagcagc |

Variable region nucleotide sequences

| | VHnu |
|---|---|
| W5626-2C2 | SEQ ID NO: 12 gaggtgcagttggtggagtctgggggaggattggtgcaggc tggggactctctgagactctcctgtgcagcctccggacgca cccacagtaactatgtcatgggctggttccgccaggctcca gggcaggagcgtgagtttgtagcaggtattagcaggactta tggtaatacatactatagagactccgtggagggccgattca ccatctccgtagacaaccccaagaacacggtgtatttgcaa atgaacagcctgaaacctgaggacacggccgtttattactg tgcagcagacccgacccgttctgaagtgatacttactactt cacaccgctatgtctactggggccaggggaccctggtcact gtctcctca |
| W5626-2C2-z22 | SEQ ID NO: 14 gaggtgcagctggtggagtccggaggaggactggtgcagcc cggaggatctttaagactgagctgcgccgccagcggcagaa cccacagcaactacgtgatgggctggttccgtcaagctccc ggtcaagagagggagttcgtggccggcatcagcaggaccta cggcaacacctactacagggacagcgtggagggtcgtttca ccatctctcgtgacaacagcaagaacactttatatttacag atgaactctttaagggccgaggacaccgccgtgtactactg cgccgctgatcccactcgtagcgaggtgattttaaccacaa gccatcgttacgtgtactggggacaaggtactttagtgacc gtgtccagc |

In certain embodiments, the antibody polypeptides provided herein are single domain antibodies.

In certain embodiments, the heavy chain variable domain of the antibody polypeptides provided herein is derived from a VHH domain. VHH domains are heavy chain variable domains derived from antibodies naturally devoid of light chains, for example, antibodies derived from Camelidae species (see, e.g. WO9404678), for example in camel, llama, dromedary, alpaca and guanaco. VHH domains are single polypeptides, and are stable.

In certain embodiments, the heavy chain variable domain of the antibody polypeptides provided herein is of camelid origin.

CDRs are known to be responsible for antigen binding, however, it has been found that not all of the 6 CDRs are indispensable or unchangeable. In other words, it is possible to replace or change or modify one or more CDRs in anti-EGFR single domain antibody W5626-2C10, or W5626-2C2, yet substantially retain the specific binding affinity to EGFR.

In certain embodiments, the anti-EGFR antibody polypeptides provided herein comprise a heavy chain CDR3 sequence of one of the anti-EGFR antibodies W5626-2C10, or W5626-2C2. In certain embodiments, the anti-EGFR antibody polypeptides provided herein comprise a heavy chain CDR3 sequence selected from the group consisting of SEQ ID NOs: 3 and 6. Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81). The diversity in the heavy chain CDR3 is sufficient to produce most antibody specificities (Xu J L, Davis M M. Immunity. 13:37-45) as well as desirable antigen-binding affinity (Schier R, etc. J Mol Biol. 263:551-67).

In certain embodiments, the antibody polypeptides provided herein comprise suitable framework region (FR) sequences, as long as the antibody polypeptides can specifically bind to EGFR. The CDR sequences provided in Table 1 are obtained from camelid antibodies, but they can be grafted to any suitable FR sequences of any suitable species such as mouse, human, rat, rabbit, among others, using suitable methods known in the art such as recombinant techniques.

In certain embodiments, the antibody polypeptides provided herein are humanized. A humanized antibody polypeptide is desirable in its reduced immunogenicity in human. A humanized antibody polypeptide is chimeric in its variable regions, as non-human CDR sequences are grafted to human or substantially human FR sequences. Humanization of an antibody polypeptide can be essentially performed by substituting the non-human (such as murine) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Suitable human heavy chain variable domains can be selected to achieve this purpose using methods known in the art. In an illustrative example, "best-fit" approach can be used, where a non-human (e.g. camelid) antibody variable domain sequence is screened or BLASTed against a database of known human variable domain sequences, and the human sequence closest to the non-human query sequence is identified and used as the human scaffold for grafting the non-human CDR sequences (see, for example, Sims et al, (1993) J. Immunol. 151:2296; Chothia et al. (1987) J. Mot. Biol. 196:901). Alternatively, a framework derived from the consensus sequence of all human antibodies may be used for the grafting of the non-human CDRs (see, for example, Carter et at. (1992) Proc. Natl. Acad. Sci. USA, 89:4285; Presta et al. (1993) J. Immunol., 151:2623).

In certain embodiments, the humanized antibody polypeptides provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived different human immunoglobulin genes, for example, FR sequences derived from one human antibody and constant region from another human antibody. In some embodiments, the humanized antibody polypeptide comprise human FR1-4.

In certain embodiments, the humanized antibody polypeptides provided herein comprise one or more FR sequences of W5626-2C10-z5 or W5626-2C2-z22.

The two exemplary humanized anti-EGFR single domain antibodies W5626-2C10-z5 or W5626-2C2-z22 both retained the specific binding affinity to EGFR (e.g. human EGFR), and are at least comparable to, or even better than, the parent camelid antibodies in that aspect.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody polypeptides closely approximate the non-human parent antibody structure. In certain embodiments, the humanized antibody polypeptides provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains.

In certain embodiments, the antibody polypeptides provided herein comprise a heavy chain variable domain sequence selected from the group consisting of SEQ ID NO: 7, SEQ ID NO: 9, SEQ ID NO: 11, and SEQ ID NO: 13.

In some embodiments, the anti-EGFR antibody polypeptides provided herein comprise all or a portion of the heavy chain variable domain. In one embodiment, the anti-EGFR antibody polypeptides provided herein is a single domain antibody which consists of all or a portion of the heavy chain variable domain provided herein. More information of such a single domain antibody is available in the art (see, e.g., U.S. Pat. No. 6,248,516).

In certain embodiments, the anti-EGFR antibody polypeptides provided herein further comprise an immunoglobulin constant region. In some embodiments, an immunoglobulin constant region comprises a heavy chain. The heavy chain constant region comprises CH1, hinge, and/or CH2-CH3 regions. In certain embodiments, the heavy chain constant region comprises an Fc region. In certain embodiments, the heavy chain constant region comprises or is a CH2-CH3 region.

In some embodiments, the anti-EGFR antibody polypeptide provided herein has a constant region of an immunoglobulin (Ig), optionally a human Ig, optionally a human IgG. The constant region can be in any suitable isotype. In certain embodiments, the anti-EGFR antibody polypeptide provided herein comprises a constant region of IgG1 isotype, which could induce ADCC or CDC, or a constant region of IgG4 or IgG2 isotype, which has reduced or depleted effector function. Effector functions such as ADCC and CDC can lead to cytotoxicity to cells expressing EGFR. The effector functions can be evaluated using various assays such as Fc receptor binding assay, C1q binding assay, and cell lysis assay.

Binding affinity of the antibody polypeptide provided herein can be represented by $K_D$ value, which represents the ratio of dissociation rate to association rate ($k_{off}/k_{on}$) when the binding between the antigen and antigen-binding molecule reaches equilibrium. The antigen-binding affinity (e.g. $K_D$) can be appropriately determined using suitable methods known in the art, including, for example, flow cytometry assay. In some embodiments, binding of the antibody polypeptide to the antigen at different concentrations can be determined by flow cytometry, the determined mean fluorescence intensity (MFI) can be firstly plotted against antibody concentration, $K_D$ value can then be calculated by fitting the dependence of specific binding fluorescence intensity (Y) and the concentration of antibodies (X) into the one site saturation equation: $Y=B_{max}*X/(K_D+X)$ using Prism version 5 (GraphPad Software, San Diego, Calif.), wherein $B_{max}$ refers to the maximum specific binding of the tested antibody polypeptide to the antigen.

Binding of the antibody polypeptides to human EGFR can also be represented by "half maximal effective concentration" ($EC_{50}$) value, which refers to the concentration of an antibody where 50% of its maximal effect (e.g., binding or inhibition etc.) is observed. The $EC_{50}$ value can be measured by methods known in the art, for example, sandwich assay such as ELISA, Western Blot, flow cytometry assay, and other binding assay.

In certain embodiments, the antibody polypeptides provided herein specifically bind to human EGFR with a $K_D$ of no more than 1 nM, no more than 1.5 nM, no more than 1.8 nM, no more than 2 nM, no more than 3 nM, no more than 5 nM, no more than 10 nM, no more than 20 nM, no more than 50 nM by flow cytometry assay, or with an $EC_{50}$ of no more than 0.8 nM, no more than 1 nM, no more than 2 nM, no more than 3 nM, no more than 4 nM, no more than 5 nM, no more than 8 nM, no more than 10 nM, or no more than 20 nM by flow cytometry assay.

In certain embodiments, the antibody polypeptides provided herein specifically bind to human EGFR extracellular domain (ECD) with a $K_D$ of no more than 0.3 nM, no more than 0.4 nM, no more than 0.5 nM, no more than 0.6 nM, no more than 0.7 nM, no more than 0.8 nM, no more than 0.9 nM, no more than 1 nM, no more than 1.5 nM, no more than 1.8 nM, no more than 2 nM, no more than 3 nM, no more than 5 nM, no more than 10 nM by Surface plasmon resonance (SPR) assay.

In certain embodiments, the antibody polypeptides provided herein specifically bind to human EGFRVIII with a $K_D$ of no more than 0.3 nM, no more than 0.4 nM, no more than 0.5 nM, no more than 0.6 nM, no more than 0.7 nM, no more than 0.8 nM, no more than 0.9 nM, no more than 1 nM, no more than 1.5 nM, no more than 1.8 nM, no more than 2 nM, no more than 3 nM, no more than 5 nM, no more than 10 nM by flow cytometry assay, or with an $EC_{50}$ of no more than 1 nM, no more than 1.5 nM, no more than 2 nM, no more than 2.5 nM, no more than 3 nM, no more than 3.5 nM, no more than 4 nM, no more than 5 nM, no more than 10 nM, or no more than 20 nM by flow cytometry assay.

In certain embodiments, the anti-EGFR antibody polypeptides provided herein cross-react with Cynomolgus monkey EGFR, or mouse EGFR. In certain embodiments, the antibody polypeptides bind to Cynomolgus monkey or mouse EGFR with a binding affinity similar to that of human EGFR. For example, binding of the exemplary single domain antibodies W5626-2C10, W5626-2C10-z5, W5626-2C2, and W5626-2C2-z22 to Cynomolgus monkey or mouse EGFR is at a similar affinity or $EC_{50}$ value to that of human EGFR.

In certain embodiments, the antibody polypeptides provided herein specifically bind to Cynomolgus monkey EGFR at an $EC_{50}$ of no more than 0.3 nM, no more than 0.5 nM, no more than 0.8 nM, no more than 1 nM, or no more than 1.5 nM, or no more than 2 nM, no more than 2.5 nM, no more than 3 nM, no more than 3.5 nM, no more than 4 nM, no more than 5 nM, no more than 5 nM, no more than 10 nM, or no more than 20 nM as measured by flow cytometry assay, or with a $K_D$ of no more than 0.3 nM, no more than 0.5 nM, no more than 0.8 nM, no more than 1 nM, or no more than 1.5 nM, or no more than 2 nM, no more than 2.5 nM, no more than 3 nM, no more than 3.5 nM, no more than 4 nM, no more than 5 nM no more than 5 nM, no more than 10 nM, or no more than 20 nM by flow cytometry assay.

In certain embodiments, the antibody polypeptides provided herein specifically bind to mouse EGFR with an $EC_{50}$ of no more than 0.6 nM, no more than 0.7 nM, no more than 0.8 nM, no more than 0.9 nM, no more than 1 nM, no more than 1.2 nM, no more than 1.5 nM, no more than 3 nM, or no more than 5 nM, or no more than 10 nM as measured by flow cytometry assay, or with a $K_D$ of no more than 0.5 nM, no more than 0.8 nM, no more than 1 nM, no more than 1.5 nM, or no more than 3 nM, no more than 5 nM, no more than 10 nM, no more than 15 nM, or no more than 20 nM by flow cytometry assay.

In certain embodiments, the antibody polypeptides provided herein have a specific binding affinity to human EGFR which is sufficient to provide for diagnostic and/or therapeutic use.

The antibody polypeptides provided herein can be monoclonal, humanized, chimeric, recombinant, labeled, bivalent, or anti-idiotypic. A recombinant antibody polypeptide is an antibody polypeptide prepared in vitro using recombinant methods rather than in animals.

Antibody Variants

The antibody polypeptides provided herein also encompass various variants thereof. In certain embodiments, the antibody polypeptides encompasses various types of variants of an exemplary antibody provided herein, i.e., W5626-2C10, W5626-2C2, W5626-2C10-z5 or W5626-2C2-z22.

In certain embodiments, the antibody polypeptide variants comprise one or more modifications or substitutions in one or more CDR sequences as provided in Table 1, one or more variable region sequences (but not in any of the CDR sequences) provided in Table 2, and/or the constant region (e.g. Fc region). Such variants retain specific binding affinity to EGFR of their parent antibodies, but have one or more desirable properties conferred by the modification(s) or substitution(s). For example, the antibody polypeptide variants may have improved antigen-binding affinity, improved productivity, improved stability, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation (e.g. one or more introduced cysteine residues).

The parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g., charged residues such as Arg, Asp, His, Lys, and Glu) can be identified and replaced by a neutral or negatively charged amino acid (e.g., alanine or polyalanine), and the modified antibody polypeptides are produced and screened for the interested property. If substitution at a particular amino acid location demonstrates an interested functional change, then the position can be identified as a potential residue for modification or substitution. The potential residues may be further assessed by substituting with a different type of residue (e.g. cysteine residue, positively charged residue, etc.).

Affinity Variant

Affinity variant may contain modifications or substitutions in one or more CDR sequences as provided in Table 1, one or more FR sequences, or the heavy chain variable region sequences provided in Table 2. FR sequences can be readily identified by a skilled person in the art based on the CDR sequences in Table 1 and variable region sequences in Table 2, as it is well-known in the art that a CDR region is flanked by two FR regions in the variable region. The affinity variants retain specific binding affinity to EGFR of the parent antibody, or even have improved EGFR specific binding affinity over the parent antibody. In certain embodiments, at least one (or all) of the substitution(s) in the CDR sequences, FR sequences, or variable region sequences comprises a conservative substitution.

A skilled artisan will understand that in the CDR sequences and variable region sequences provided in Table 1 and Table 2, one or more amino acid residues may be substituted yet the resulting antibody polypeptide still retain the binding affinity to EGFR, or even have an improved binding affinity. Various methods known in the art can be used to achieve this purpose. For example, a library of antibody variants (such as Fab or scFv variants) can be generated and expressed with phage display technology, and then screened for the binding affinity to human EGFR. For another example, computer software can be used to virtually simulate the binding of the antibodies to human EGFR, and identify the amino acid residues on the antibodies which form the binding interface. Such residues may be either avoided in the substitution so as to prevent reduction in binding affinity, or targeted for substitution to provide for a stronger binding.

In certain embodiments, the humanized antibody polypeptides provided herein comprise one or more amino acid residue substitutions in one or more CDR sequences, and/or one or more FR sequences. In certain embodiments, an affinity variant comprises no more than 10, 9, 8, 7, 6, 5, 4, 3, 2, or 1 substitutions in the CDR sequences and/or FR sequences in total.

In certain embodiments, the anti-EGFR antibody polypeptides comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to EGFR at a level similar to or even higher than its parent antibody.

In certain embodiments, the anti-EGFR antibody polypeptides comprise one or more variable region sequences having at least 80% (e.g. at least 85%, 88%, 90%, 91%, 92%, 93%, 94%, 95%, 96%, 97%, 98%, 99%) sequence identity to that (or those) listed in Table 2, and in the meantime retain the binding affinity to EGFR at a level similar to or even higher than its parent antibody. In some embodiments, a total of 1 to 10 amino acids have been substituted, inserted, or deleted in a variable region sequence listed in Table 2. In some embodiments, the substitutions, insertions, or deletions occur in regions outside the CDRs (e.g., in the FRs).

Glycosylation Variant

The anti-EGFR antibody polypeptides provided herein also encompass a glycosylation variant, which can be obtained to either increase or decrease the extent of glycosylation of the antibody polypeptide.

The antibody polypeptide may comprise one or more amino acid residues with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

Cysteine-Engineered Variant

The anti-EGFR antibody polypeptides provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibody polypeptides to introduce free cysteine residues are known in the art, see, for example, WO2006/034488.

Fc Variant

The anti-EGFR antibody polypeptides provided herein also encompass an Fc variant, which comprises one or more amino acid residue modifications or substitutions at its Fc region and/or hinge region.

In certain embodiments, the anti-EGFR antibody polypeptides comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody polypeptide to improve binding affinity with FcRn are well-known in the art, see, for example, Vaughn, D. et al, Structure, 6(1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70: 3269-3277 (2010); and Hinton, P. et al, J. Immunology, 176:346-356 (2006).

In certain embodiments, the anti-EGFR antibody polypeptides comprise one or more amino acid substitution(s) that alters the antibody-dependent cellular cytotoxicity (ADCC). Certain amino acid residues at the Fc region (e.g. at the CH2 domain) can be substituted to provide for altered (e.g. enhanced, decreased, or depleted) ADCC activity. Alternatively or additionally, carbohydrate structures on the antibody can be changed to alter (e.g. enhance, decrease, or deplete) ADCC activity. Methods of altering ADCC activity by antibody engineering have been described in the art, see for example, Shields R L. et al., J Biol Chem. 2001. 276(9): 6591-604; Idusogie E E. et al., J Immunol. 2000.164(8): 4178-84; Steurer W. et al., J Immunol. 1995, 155(3): 1165-74; Idusogie E E. et al., J Immunol. 2001, 166(4): 2571-5; Lazar G A. et al., PNAS, 2006, 103(11): 4005-4010; Ryan M C. et al., Mol. Cancer Ther., 2007, 6: 3009-3018; Richards J O. et al., Mol Cancer Ther. 2008, 7(8): 2517-27; Shields R. L. et al, J. Biol. Chem, 2002, 277: 26733-26740; Shinkawa T. et al, J. Biol. Chem, 2003, 278: 3466-3473.

In certain embodiments, the anti-EGFR antibody polypeptides comprise one or more amino acid substitution(s) that alters Complement Dependent Cytotoxicity (CDC), for example, by improving or diminishing C1q binding and/or CDC (see, for example, WO99/51642; Duncan & Winter Nature 322:738-40 (1988); U.S. Pat. Nos. 5,648,260; 5,624, 821); and WO94/29351 concerning other examples of Fc region variants.

In certain embodiments, the anti-EGFR antibody polypeptides comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g., as described in U.S. Pat. No. 5,731,168.

Various techniques can be used for the production of VHH or single domain antibodies. For example, VHHs may be obtained using methods known in the art such as by immunising a camel and obtaining hybridomas therefrom, or by cloning a library of single domain antibodies using molecular biology techniques known in the art and subsequent selection by using phage display.

In another aspect of the present disclosure, an antibody polypeptide provided herein may comprise two or more single domain antibodies which have been joined. The single domain antibodies may be identical in sequence and directed against the same target or antigen. Depending on the number of VHHs linked, the antibody polypeptide may be bivalent (2 VHHs), trivalent (3 VHHs), tetravalent (4 VHHs) or have a higher valency molecules.

Conjugates

In some embodiments, the anti-EGFR antibody polypeptides further comprise a conjugate moiety. The conjugate moiety can be linked to the antibody polypeptides. A conjugate moiety is a non-proteinaceous moiety that can be attached to the antibody polypeptide. It is contemplated that a variety of conjugate moieties may be linked to the antibody polypeptides provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibody polypeptides by covalent binding, affinity binding, intercalation, coordinate binding, complexation, association, blending, or addition, among other methods.

In certain embodiments, the antibody polypeptides disclosed herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

In certain embodiments, the antibodies may be linked to a conjugate moiety indirectly, or through another conjugate moiety. For example, the antibody polypeptides may be conjugated to biotin, then indirectly conjugated to a second conjugate that is conjugated to avidin. The conjugate can be a clearance-modifying agent, a toxin (e.g., a chemotherapeutic agent), a detectable label (e.g., a radioactive isotope, a lanthanide, a luminescent label, a fluorescent label, or an enzyme-substrate label), or purification moiety.

A "toxin" can be any agent that is detrimental to cells or that can damage or kill cells. Examples of toxin include, without limitation, taxol, cytochalasin B, gramicidin D, ethidium bromide, emetine, mitomycin, etoposide, tenoposide, vincristine, MMAE, MMAF, DM1, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), a topoisomerase inhibitor, and a tubulin-binders.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides), luminescent labels, chromophoric moiety, digoxigenin, biotin/avidin, a DNA molecule or gold for detection.

In certain embodiments, the conjugate moiety can be a clearance-modifying agent which helps increase half-life of the antibody. Illustrative example include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead.

In certain embodiments, the antibody polypeptides provided herein is used for a base for a conjugate.

Polynucleotides and Recombinant Methods

The present disclosure provides polynucleotides that encode the anti-EGFR antibody polypeptides.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

In certain embodiments, the polynucleotides comprise one or more nucleotide sequences as shown in SEQ IN NO: 8, 10, 12, and/or 14, and/or a homologous sequence thereof having at least 80% (e.g. at least 85%, 88%, 90%, 91%, 92%, 93%, 94%, 95%, 96%, 97%, 98%, 99%) sequence identity, and/or a variant thereof having only degenerate substitutions, and encodes the variable region of the exemplary antibodies provided herein. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The isolated polynucleotide that encodes the anti-EGFR antibody polypeptides (e.g. including the sequences as shown in Table 3) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

The present disclosure provides vectors (e.g., expression vectors) containing the nucleic acid sequence provided herein encoding the antibody polypeptides, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody polypeptide can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Envinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for expressing anti-EGFR antibody polypeptides. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TM cells (Mather et al., *Annals N.Y. Acad. Sci.* 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-EGFR antibody polypeptide production and cultured in conventional nutrient media modified as appropriate for inducing promoters, selecting transformants, or amplifying the genes encoding the desired sequences. In another embodiment, the antibody polypeptides may be produced by homologous recombination known in the art.

The host cells used to produce the antibody polypeptides provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody polypeptides can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-EGFR antibody polypeptides prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody polypeptide. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., *J. Immunol. Meth.* 62:1-13 (1983)). Protein G is recommended for all mouse isotypes and for human gamma3 (Guss et al., *EMBO J.* 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Composition

The present disclosure further provides pharmaceutical compositions comprising the anti-EGFR antibody polypeptides and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody polypeptide and conjugates as provided herein decreases oxidation of the antibody polypeptide. This reduction in oxidation prevents or reduces loss of binding affinity, thereby improving antibody stability and maximizing shelf-life. Therefore, in certain embodiments compositions are provided that comprise one or more antibody polypeptides as disclosed herein and one or more antioxidants such as methionine. Further provided are methods for preventing oxidation of, extending the shelf-life of, and/or improving the efficacy of an antibody polypeptide as provided herein by mixing the antibody polypeptide with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody polypeptide as disclosed herein in a suitable solvent. The solvent may contain an excipient which improves the stability or other pharmacological components of the powder or reconstituted solution, prepared from the powder. Excipients that may be used include, but are not limited to, water, dextrose, sorbitol, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-EGFR antibody polypeptides or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Methods of Use

The present disclosure also provides therapeutic methods comprising: administering a therapeutically effective amount of the antibody polypeptides as provided herein to a subject in need thereof, thereby treating or preventing an EGFR-related condition or a disorder. In some embodiment, the EGFR-related condition or a disorder is cancer, or inflammatory disease.

Examples of cancer include but are not limited to, lymphoma, bladder cancer, bone cancer, brain and central nervous system cancer, breast cancer, uterine or endometrial cancer, rectal cancer, esophageal cancer, head and neck cancer, anal cancer, gastrointestinal cancer, intra-epithelial neoplasm, kidney or renal cancer, leukemia, liver cancer, lung cancer (e.g. non-small cell lung cancer and small cell lung cancer), melanoma, myeloma, pancreatic cancer, prostate cancer, sarcoma, skin cancer, squamous cell cancer, stomach cancer, testicular cancer, vulval cancer, cancer of the endocrine system, cancer of the parathyroid gland, cancer of the adrenal gland, penile carcinoma, solid tumors of childhood, tumor angiogenesis, spinal axis tumor, pituitary adenoma, or epidermoid cancer.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, psoriasis, sepsis, stroke, transplantation of tissue and organs, vasculitis, diabetic retinopathy and ventilator induced lung injury.

In certain embodiments, the EGFR-related condition or a disorder is also associated with EGFR variant III (EGFRvIII), for example, glioblastoma.

In some embodiments, the subject has been identified as being likely to respond to an EGFR antibody. The presence, level, subtype and/or mutation of EGFR on an interested biological sample can be indicative of whether the subject from whom the biological sample is derived could likely respond to an EGFR antibody. Various methods can be used to determine the presence, level, subtype and/or mutation of EGFR in a test biological sample from the subject. For example, the test biological sample can be exposed to anti-EGFR antibody or antigen-binding fragment thereof, which binds to and detects the expressed EGFR protein. Alternatively, EGFR can also be detected at nucleic acid expression level, using methods such as qPCR, reverse transcriptase PCR, microarray, SAGE, FISH, and the like. In some embodiments, the test sample is derived from a cancer cell or tissue, or tumor infiltrating immune cells. In certain embodiments, presence or up-regulated level of the EGFR in the test biological sample indicates likelihood of responsiveness. The term "up-regulated" as used herein, refers to an overall increase of no less than 10%, 15%, 20%, 25%, 30%, 35%, 40%, 45%, 50%, 55%, 60%, 65%, 70%, 75%, 80% or greater, in the protein level of EGFR in the test sample, as compared to the EGFR protein level in a reference sample as detected using the same method. The reference sample can be a control sample obtained from a healthy or non-diseased individual, or a healthy or non-diseased sample obtained from the same individual from whom the test sample is obtained. For example, the reference sample can be a non-diseased sample adjacent to or in the neighborhood of the test sample (e.g. tumor).

The therapeutically effective amount of an antibody polypeptide as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the antibody polypeptides as provided herein may be administered at a therapeutically effective dosage of about 0.01 mg/kg to about 100 mg/kg. In certain of these embodiments, the antibody polypeptide is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibody polypeptides disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the antibody polypeptides disclosed herein may be administered alone or in combination with one or more additional therapeutic means or agents. For example, the antibody polypeptides disclosed herein may be administered in combination with another therapeutic agent, for example, a chemotherapeutic agent or an anti-cancer drug.

In certain of these embodiments, an antibody polypeptide as disclosed herein that is administered in combination with one or more additional therapeutic agents may be administered simultaneously with the one or more additional therapeutic agents, and in certain of these embodiments the antibody polypeptide and the additional therapeutic agent(s) may be administered as part of the same pharmaceutical composition. However, an antibody polypeptide administered "in combination" with another therapeutic agent does not have to be administered simultaneously with or in the same composition as the agent. An antibody polypeptide administered prior to or after another agent is considered to be administered "in combination" with that agent as the phrase is used herein, even if the antibody polypeptide and second agent are administered via different routes. Where possible, additional therapeutic agents administered in combination with the antibody polypeptides disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of using the anti-EGFR antibody polypeptides.

In some embodiments, the present disclosure provides methods of detecting presence or amount of EGFR in a sample, comprising contacting the sample with the antibody polypeptide, and determining the presence or the amount of EGFR in the sample.

In some embodiments, the present disclosure provides methods of diagnosing a EGFR related disease or condition in a subject, comprising: a) contacting a sample obtained from the subject with the antibody polypeptide provided herein; b) determining presence or amount of EGFR in the sample; and c) correlating the existence of the EGFR to the EGFR related disease or condition in the subject.

In some embodiments, the present disclosure provides kits comprising the antibody polypeptide provided herein, optionally conjugated with a detectable moiety. The kits may be useful in detection of EGFR or diagnosis of EGFR related disease.

In some embodiments, the present disclosure also provides use of the antibody polypeptide provided herein in the manufacture of a medicament for treating an EGFR related disease or condition in a subject, in the manufacture of a diagnostic reagent for diagnosing a EGFR related disease or condition.

Advantages

The present disclosure provides herein anti-EGFR therapeutic antibody polypeptides. The antibody polypeptides (e.g. VHH antibodies, humanized VHH antibodies and the Fc fusions thereof) provided herein cross-react to mouse and monkey EGFR, which could facilitate anti-tumor efficacy studies in mouse syngeneic tumor models and allow appropriate preclinical testing. In addition, the antibody polypeptides provided herein also recognize EGFR variant III (EGFRvIII) with high affinity, which is present in about 25% to 30% of glioblastoma cases. The antibody polypeptides provided herein showed high potency in competitive blocking of EGF binding thus preventing down-stream signaling. The antibody polypeptides provided herein could also induced EGFR internalization with high efficacy. In conclusion, the antibody polypeptides provided herein are excellent therapeutic antibody candidates, which can also be used for the development of antibody-drug conjugates and as building blocks for bispecific antibody application.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1: Generation of Antigen, Antibodies and Cell Lines

1. Preparation of Human EGFR, Human EGFRvIII, *Macaca fascicularis* EGFR and Mouse EGFR ECD Proteins The gene encoding extracellular domain (ECD) of human EGFR or EGFRvIII was inserted into expression vector pcDNA 3.3 with a 6-Histidine (6×His) tag or human Fc (hFc) fused at the C-terminus of EGFR ECD. The gene encoding *Macaca fascicularis* EGFR (monkey EGFR) ECD was inserted into expression vector pcDNA 3.3 with human Fc (hFc) fused at the C-terminus of EGFR ECD. The gene encoding mouse EGFR ECD was inserted into pcDNA 3.3 with human Fc (hFc) fused at the C-terminus of EGFR ECD. The plasmids were transfected into HEK293 cells using PlasFect (Bioline). The 6×His-tagged proteins were purified from harvested supernatant using a Ni column, followed by ion-exchange column. The hFc-fused proteins were purified using a Protein A column.

2. Preparation of Benchmark Antibodies

Reference benchmark antibody Erbitux (W562-BMK2) is a chimeric monoclonal IgG1 antibody from commercial sources. W562-BMK3 was generated based on the sequence of huML66 in Patent US20140023662. The plasmids pcDNA3.4 containing VH and VL genes were co-transfected into HEK293 cells, and the culture supernatant was harvested for purification. Erbitux-scFv (which does not contain Fc region) antibody was generated by gene synthesis of VH-(G4S)3-VL gene in Sangon Biotech (Shanghai, China), and then subcloned into modified pcDNA 3.3 expression vector with c-myc and 6×his tag. Then the plasmids were transfected into Expi293 cells. Cells were cultured for 5 days and supernatant was collected for protein purification using Protein A column (GE Healthcare, 175438) or Protein G column (GE Healthcare, 170618). The obtained antibodies were analyzed by SDS-PAGE and SEC, and then stored at −80° C.

3. Antibody Purification

The transfected cell culture supernatants were harvested and loaded to Protein A column after adjusting pH to 7.0. Antibodies were eluted by Glycine-HCl (pH 2.5) followed by immediately neutralization using 1 M Tris. Antibody concentration was measured by Nano Drop. The purity of proteins was evaluated by SDS-PAGE and analytic HPLC-SEC (TOSOH-0008541).

4. Preparation of Human, Monkey and Mouse EGFR Expressing CHO-K1 Engineered Cell Lines The full length genes of human EGFR, human EGFRvIII, *Macaca fascicularis* EGFR and mouse EGFR were respectively inserted into expression vector pcDNA 3.3 and then transfected into CHO-K1 cells by Lipofectamine 2000 (Invitrogen), respectively. The cells were cultured in medium containing proper selection pressure. Stable single cell clones were isolated by limiting dilution and screened by FACS using anti-EGFR antibodies. The following stable cell lines expressing EGFR were selected: W562-CHO-K1.hPro1.E9 expressing human EGFR; W562-CHO-K1.hPro3.A5B2 expressing human EGFRvIII; W562-CHO-K1.cynoPro1.H6 expressing monkey EGFR; W562-CHO-K1.mPro1.F3 expressing mouse EFGR.

5. Cultivation of Cell Lines

T-75 flasks and complete growth medium F12-K with 10% FBS and 8 µg/ml Blasticidin were used for subcultivation of EGFR expressing CHO-K1 cell lines. DMEM medium with 10% FBS was for A431 cell line. The subcultivation ratio 1:6 to 1:20 was used for CHO-K1 cells and 1:3 to 1:8 for A431 cell line. Medium was renewed every 2 to 3 days and Trypsin-EDTA solution was used for detaching the cells. For long term storage, the cells were frozen in complete growth medium supplemented with 5% (v/v) DMSO and stored in liquid nitrogen vapor phase.

Example 2: Generation of VHH and VHH-Fc

1. Immunization

To induce a humoral immune response towards EGFR in camelid animals, the animals were subcutaneously injected with recombinant hFc tagged human EGFR ECD proteins with intervals of 1 to 3 weeks and the dose ranged from 50 ug to 200 ug per injection for totally 6-8 doses.

2. Serum Titer Detection

The presence of anti-EGFR antibody in sera was determined by flow cytometry with EGFR expressing CHO-K1 cell lines and control CHO-K1 cells. W562-CHO-K1.hPro1.E9 and W562-CHO-K1.mPro1.F3 cell lines were used for detecting anti-human EGFR and anti-mouse EGFR titers, respectively. The cells were firstly incubated with serial dilutions of pre-immune or immune sera in 96-well U-bottom plates (BD, Franklin Lakes, N.J., USA) at a density of $1\times10^5$ cells/well at 4° C. for 1 h, then followed by FITC conjugated Goat Anti-Llama IgG antibody (Novas Biologicals, Littleton, Colo., USA) at 4° C. in the dark for 30 min. 2 times of washes were applied between each step and finally the cells were resuspended in 1×PBS/1% BSA for flow cytometery analysis (Intellicyt, Albuquerque, N. Mex., USA).

3. Library Construction 50 ml blood samples were collected at 6-7 days after the last two injections, respectively. Peripheral blood mononuclear cells (PBMCs) were purified by density gradient centrifugation in Ficoll-Paque PLUS (GE Healthcare, Little Chalfont, UK), resulting in the isolation of approximately $8\times10^7$ PBMCs. Total RNA was extracted from these PBMCs and transcribed into cDNA using oligo-dT and random primers and SuperScript III First-Strand Synthesis Super-Mix System (Invitrogen, Carlsbad, Calif., USA) according to the manufacturers' recommendations.

The purified cDNA was then used as template to amplify the repertoire of Ig heavy chain-encoding gene segments with the use of signal peptide domain specific primers and CH2 domain specific primers. This amplification resulted in PCR fragments of approximately 900 bp (representing conventional IgG) and 700 bp (representing heavy-chain only IgG that lack a CH1 domain). The two classes of heavy chain encoding genes were then size-separated on agarose gels and the genes encoding heavy-chain only IgG were purified by QIAquick Gel Extraction Kit (Qiagen, Hilden, Germany). The purified fragments were used as templates to amplify the VHH repertoire with the use of framework1 (FR1) and framework4 (FR4) specific primer pairs. This amplification procedure introduced a Sfi I restriction site at the 5' end of FR1 and a Not I restriction site at the 3' end of FR4. The repertoire of PCR-amplified VHH genes of about 300-400 bp were loaded on agarose gels and purified by QIAquick Gel Extraction Kit. The purified fragments were then cut with Sfi I and Not I and purified by QIAquick PCR Purification Kit (Qiagen, Hilden, Germany). The VHH gene fragments were finally ligated in phagemid vector pFL249 and electrotransformed into E. coli TG1. After electroporation, the E. coli TG1 cells were cultured in 2 ml SOC medium at 37° C. with shaking 200 rpm for 1 h, then the E. coli TG1 were plated I onto 2YT plates containing 100 ug/ml carbenicillin and 1% (w/v) glucose, and cultured at 37° C. overnight. The next day, the colonies were scraped into liquid 2YT medium with 1/3 (v/v) of 80% glycerol and stored at −80° C.

4. Panning

To select VHH fragments that would effectively bind to conformational EGFR expressed on cell surface, the methods of cell panning was employed. Firstly, $10^{12}$ cfu phages were pre-incubated with $2\times10^6$-$1\times10^7$ CHO-K1 cells for depletion of non-specific bound phage particles. Then the depleted phages were incubated with $2\times10^6$-$1\times10^7$ EGFR transfected CHO-K1 cells at 4° C. for 1 h with tumbling at 12 rpm. After washing with ice cold 5% FBS-PBS, the cell bound phage particles were eluted by Glycine-HCl (pH2.2) and then neutralized by 1M Tris-HCl (pH8.0). The eluted phage particles were used for infection of exponentially growing TG1 cells. Half of the infected TG1 cells were plated on 2YT agar plates containing 2% (w/v) glucose and 100 µg/ml ampicillin and cultured overnight at 37° C. On the next day, the colonies were scraped off from the plate and infected with helper phage M13K07 in 2YT medium with 50 µg/ml kanamycin and 100 µg/ml ampicillin for phage rescue. The rescued phages were used as the input for the next round of panning. In order to fish out the phage particles that would cross-react to monkey and mouse EGFR, the alternate panning with human EGFR and monkey/mouse EGFR CHO-K1 cell lines were used.

5. Screening

After desired panning steps, phage infected TG1 cell colonies grown on the plates were scraped off and pFL249 phagemid containing VHH fragments were extracted using NucleoSpin® Plasmid (Macherey-Nagel). The VHH fragments were cloned by digestion of pFL249 plasmids with Sfi I and Not I (NEB) and then ligated into expression vector pETbac, which containing genes of 6-his and c-Myc-tag fused at the C-terminus of VHH genes. The ligation products were transformed into E. coli BL21 (DE3) competent cells (TIANGEN) and then cultured in ZYM-5052 medium at 25° C. for 48 h with shaking at 230 rpm. The E. coli BL21 culture was centrifuged at 4000 rpm for 20 min to collect the supernatant. The supernatants were screening by FACS binding assay for identifying anti-EGFR positive VHH clones. Briefly, the E. coli supernatants were incubated with A431 cells in 96-well U-bottom plates (BD) at a density of $1\times10^5$ cells/well at 4° C. for 1 hour, then followed by incubation with Mouse Anti-c-Myc-biotin (Sigma) for 30 minutes and subsequently streptavidin PE (eBioscience) for 30 minutes at 4° C. Washes with 1% BSA-PBS were applied between each step. Finally, after washing and resuspended in 1% BSA-PBS, MFI of the cells was measured by flow cytometry (Intellicyt) and analyzed by FlowJo.

6. Sequencing

The positive E. coli clones selected by ELISA and FACS screening were sent to Biosune (Shanghai, China) for nucleotide sequencing of VHH gene. The sequencing results were analyzed using CLC Main Workbench (Qiagen, Hilden, Germany).

7. VHH Protein Production

The BL21 E. coli clones harboring VHH gene were cultured in 40 ml of ZYM-5052 medium at 25° C. for 48 h with shaking at 230 rpm. The expression of his- and c-Myc-tag fused VHH protein in BL21 supernatant was confirmed by SDS-PAGE, and then purified using Ni-NTA column. The purity of VHH was determined by SDS-PAGE and analytic SEC-HPLC. For low supernatant expression clones, ultrasonic (Scientz, Ningbo, China) breaking E. coli cells was used to release soluble VHH proteins and whole cell lysates were purified. Two VHH antibodies were so obtained, namely W5626-2C2 and W5626-2C10, and referred to as "W5626-2C2.VHH" and "W5626-2C10.VHH" in the examples and figures as appropriate.

8. Chimeric VHH-Fc (hIgG1) Protein Production

The clones of interest (e.g. W5626-2C2, W5626-2C10) were converted to VHH-Fc (hIgG1) fusion antibodies, abbreviated as VHH-IgG. Briefly, the VHH genes were PCR amplified from the pET-bac vectors using VHH-specific cloning primers containing appropriate restriction sites then cloned by fusion into a modified human Fc (IgG1) expression pcDNA3.3 vector to create corresponding clones of VHH-Fc (hIgG1) chimeric antibody. 293F cells were transiently transfected with the vector for antibody expression. The cell culture supernatants containing antibodies were harvested and purified using Protein A chromatography.

9. Humanization

"Best Fit" approach was used to humanize VHH chains. Amino acid sequences of VHH framework regions were blasted against human germline V-gene database, and humanized VHH sequences were generated by replacing human CDR sequences in the top hit with VHH CDR sequences using Kabat CDR definition. Several residues in the framework region were back-mutated to VHH in order to maintain the affinity. Humanized genes, which were back-translated and codon optimized for mammalian expression, were synthesized by GENEWIZ. These genes were re-amplified with cloning primers containing appropriate restriction sites and cloned into a modified pcDNA3.3 vector to express bivalent humanized VHHs linked with human IgG1 Fc region. Two humanized clones W5626-2C2-z22 and W5626-2c10-z5 were obtained, and expressed with human Fc of IgG1 isotype. In the following examples and figures, for VHH antibody W5626-2C2, its humanized version further comprising a human Fc of IgG1 isotype was referred to as "W5626-2C2-z22" for short, and for VHH antibody W5626-2C10, its humanized version further comprising a human Fc of IgG1 isotype is referred to as "W5626-2C10-z5" for short.

Example 3: In Vitro Characterization

1. Target FACS Binding Assay

Figure 1D:
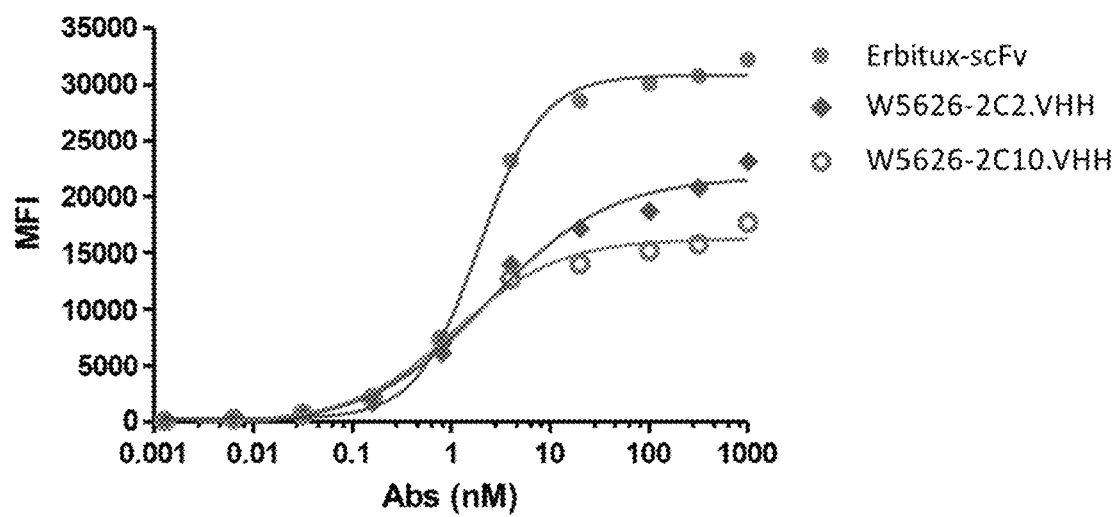
FIG. 1D shows that W5626-2C10.VHH and W5626-2C2.VHH bind to human EGFRVIII with an $EC_{50}$ (1.08 nM and 2.41 nM, respectively) similar to Erbitux-scFv as measured by FACS.

The binding of antibodies to cell surface EGFR was assessed by FACS with EGFR transfected cells and A431 cell line, which over expresses human EGFR. $1 \times 10^5$ cells/well were plated in a 96-well plate and centrifuged at 210 g for 5 minutes at 4° C. After removing the supernatant, the cell pellets were re-suspended with serial dilutions of testing purified antibodies in 1% BSA-PBS and incubated for 1 hour at 4° C., followed by incubation with FITC conjugated goat anti-human IgG (Jackson ImmunoResearch) at 4° C. for 1 hour. Two times of washing with 200 µl/well 1% BSA-PBS were applied between each step. Finally, the cells were resuspended in 100 µl 1% BSA-PBS for flow cytometry analysis (Intellicyt). As shown in FIG. 1, W5626-2C2-z22 and W5626-2C10-z5 bound to cell surface human (FIG. 1A), monkey (FIG. 1B) and mouse (FIG. 1C) EGFR in a dose dependent manner. The bindings of W5626-2C10.VHH and W5626-2C2.VHH (c-Myc and his-tagged VHH fragments) to EGFR-vIII transfected cells were tested by Mouse Anti-c-Myc-biotin (Sigma) and streptavidin-PE (eBioscience). c-Myc and his-tagged Erbitux-scFv was used as positive control. The result shows that W5626-2C2.VHH and W5626-2C10.VHH bind to cell surface human EGFR-vIII in a dose dependent manner (FIG. 1D).

2. EGF-Competition FACS Assay

Figure 2:
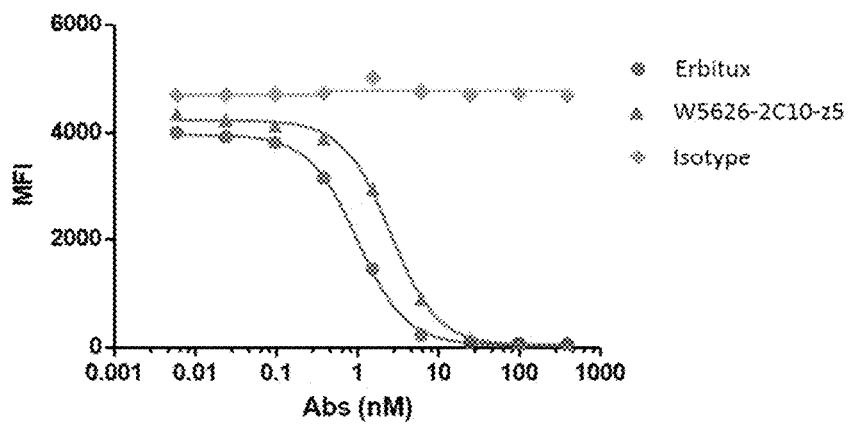
FIG. 2 shows that W5626-2C10-z5 and W5626-2C2-z22 compete EGF binding with $IC_{50}$ (2.58 nM and 1.35 nM, respectively) similar to that of Erbitux.
Figure 2:
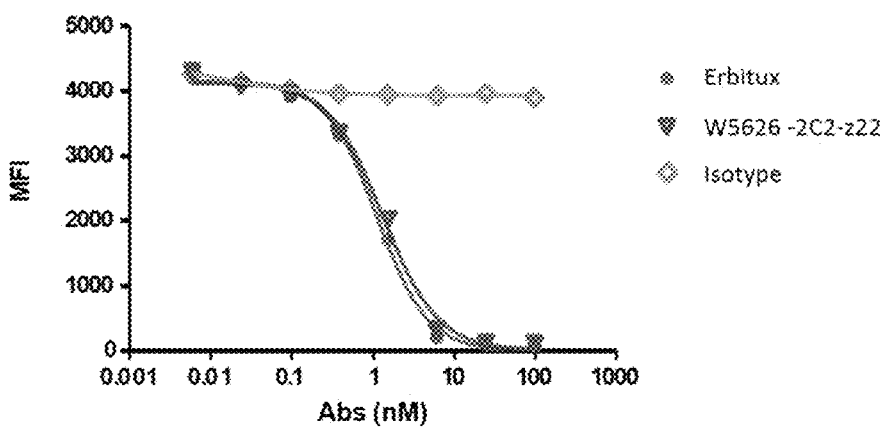

EGFR-expressing A431 cells were routinely maintained in DMEM containing 10% FBS, 10 mM HEPES and L-glutamine. $10^5$ cells per well were added to each well of a 96-well plate and centrifuged at 210 g for 5 minutes at 4° C. before the supernatant was removed. Serial dilutions of test antibodies were added to the pelleted cells and incubated for 1 hour at 4° C. The cells were washed twice and then mixed with EGF-biotin (Invitrogen, E-3477) of 50 ng/ml in 1% BSA-PBS and incubated at 4° C. for 45 minutes. Streptavidin-PE was used to detect the binding of EGF onto the cells. MFI of the cells was measured by flow cytometry and analyzed by FlowJo. Results showed in FIG. 2 indicated that W5626-2C2-z22 and W5626-2C10-z5 could compete EGF binding to cell surface EGFR with $IC_{50}$ similar to that of Erbitux.

3. Phosphorylated EGFR (pEGFR) ELISA

Figure 3:
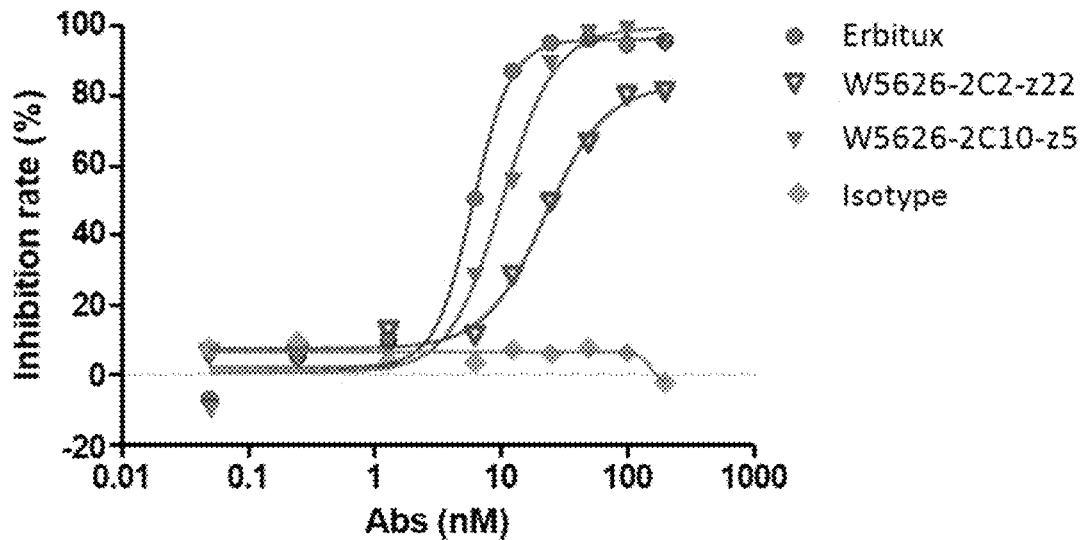
FIG. 3 shows that W5626-2C10-z5 and W5626-2C2-z22 inhibit EGFR phosphorylation at an $IC_{50}$ of 10.4 nM and 22.6 nM respectively as measured by ELISA.

EGFR-expressing A431 cells were routinely maintained in complete media (DMEM containing 10% FBS, 10 mM HEPES and L-glutamine). The cells were harvested and resuspended in complete media at a final concentration of $5 \times 10^5$ cells/mL. A volume of 100 µl cell suspension were added into each well of a 96-well flat bottom plate to give a final density of $5 \times 10^4$ cells/well. The cells were allowed to attach for approximately 5 hours before the media were exchanged with starvation media (DMEM containing 0.1% BSA). The plates were then incubated overnight at 37° C. prior to treatment with serial dilutions of anti-EGFR antibodies for 3 hours at 37° C. After the antibody treatment, the cells were treated with 25 ng/ml EGF for the final 15 mins to stimulate EGFR phosphorylation. After washing with ice-cold PBS, the cells were lysed in 100 ul/well lysis buffer (R&D Systems, catalog number DYC002) for 15 mins on ice. The lysates were collected and spinned at 1800 g for 15 minutes at 4° C. to remove cell debris. Then a sandwich ELISA was performed using the cell lysis to measure phosphorylated EGFR according to the manufacturer's instructions (R&D Systems, DYC1095B-5). The $IC_{50}$ was calculated by using GraphPad Prism 5 software (GraphPad Software, La Jolla, Calif.). The results show that W5626-2C2-z22 and W5626-2C10-z5 can inhibit EGFR phosphorylation with $IC_{50}$ of 10.4 nM and 22.6 nM, respectively (FIG. 3).

4. Fab-Zap Assay

Figure 4:
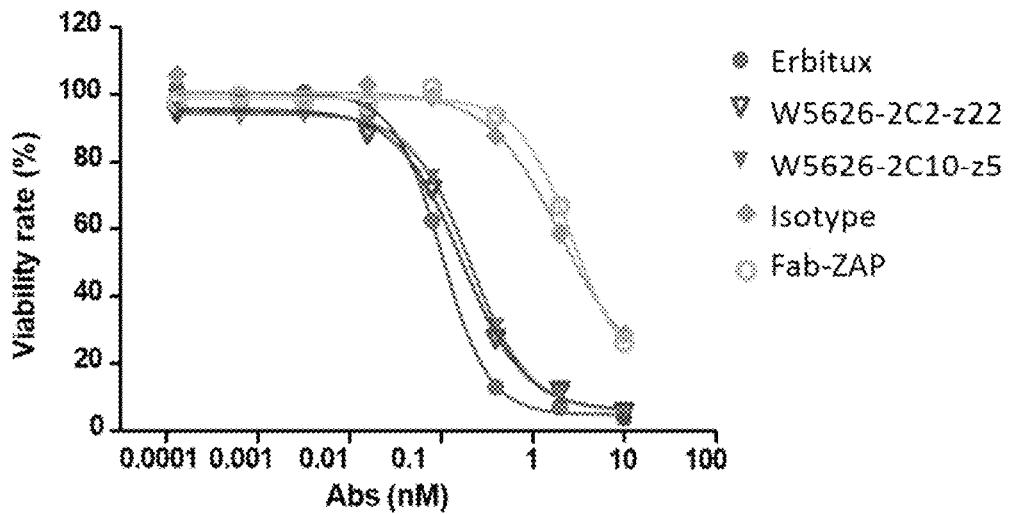
FIG. 4 shows that W5626-2C10-z5 and W5626-2C2-z22 induce EGFR internalization with $EC_{50}$ (0.21 nM and 0.17 nM respectively) similar to Erbitux using Fab-ZAP.

Fab-ZAP (Advanced Targeting Systems, Kit51) was used for testing the internalization ability of human IgG Abs. Briefly, A431 cells were plated at 5000 cells per well into 96-well clear bottom black plates (Greiner, 655090) in 50 µl DMEM complete medium containing 10% FBS and cultured overnight. On the next day, the purified Abs and Fab-Zap reagent were mixed at a ratio of Fab-Zap: Ab=3:1 (unit: mol/l) and incubated for 30 minutes at 37° C. The Ab-Fab-Zap complex was then serially diluted with assay medium and added to the A431 cells in 96 well plates. The cells were kept in a 37° C., 5% $CO_2$ incubator for 4 days and then assessed for cell viability using Cell Titer-Glo (Promega, G7573). 50 µl of Cell Titer-Glo solution was added to each well and incubated at room temperature with gentle shaking for 10 minutes. The amount of luminescence was determined using Envision (PerkinElmer). As shown in FIG. 4, W5626-2C2-z22 and W5626-2C10-z5 induce EGFR internalization with an $EC_{50}$ similar to that of Erbitux.

5. Epitope Binning

VHH fragments of W5626-2C2 and W5626-2C10 were binned against benchmark antibodies by FACS. Erbitux (human IgG1) of 0.15 m/ml and BMK3 (human IgG1) of 1 µg/ml were respectively pre-mixed with serial dilutions of purified W5626-VHH proteins. Then the mixtures were added to A431 cells and incubated for 1 hour at 4° C. After washing, the secondary antibody FITC-conjugated goat anti-human IgG (Jackson ImmunoResearch) was added to the cells and incubated at 4° C. for 1 hour. MFI of the cells were measured by flow cytometry and analyzed by FlowJo.

Figure 5A:
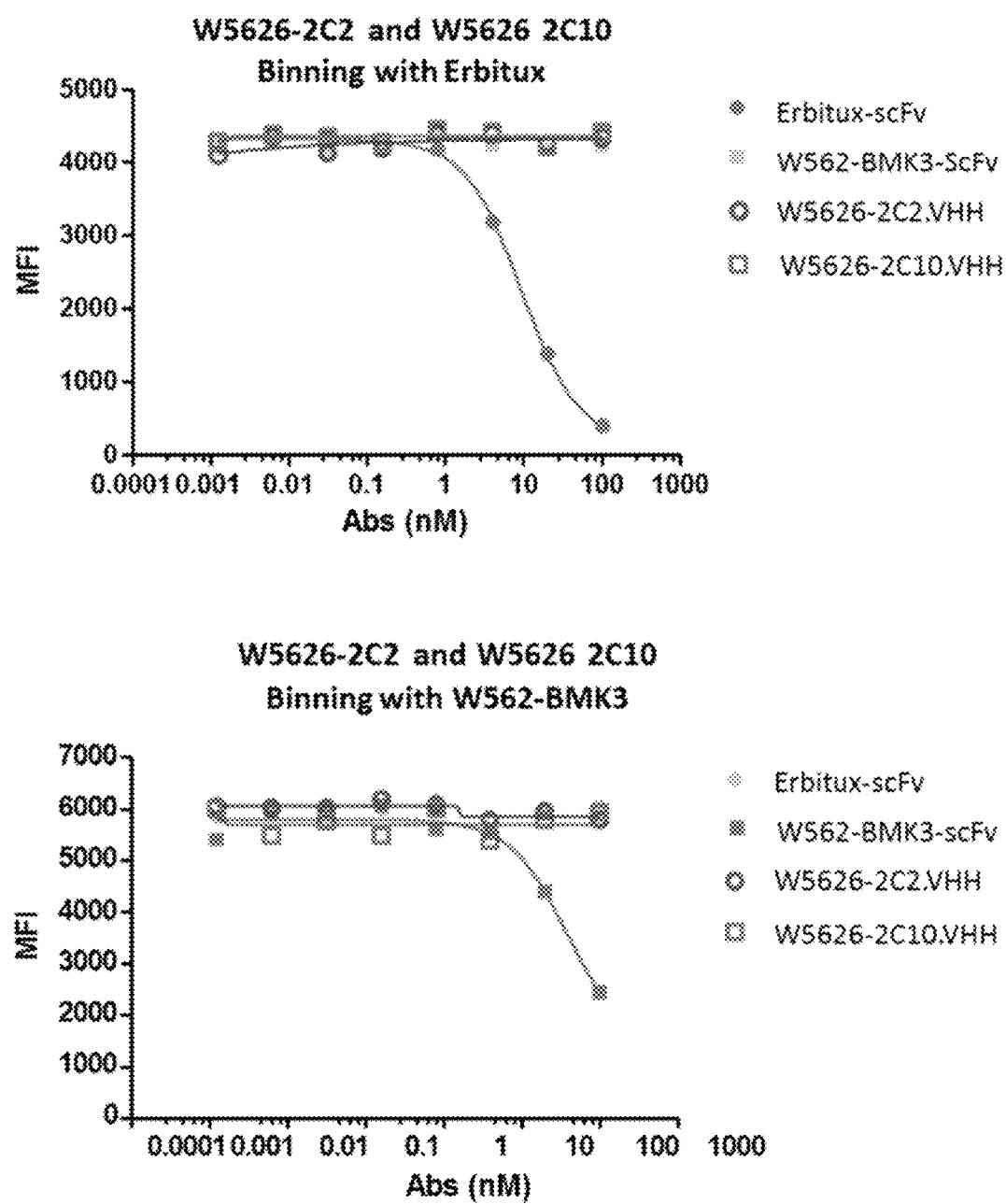
FIG. 5A shows the epitope binning test of W5626-2C10.VHH and W5626-2C2.VHH with Erbitux and W562-BMK3.
Figure 5B:
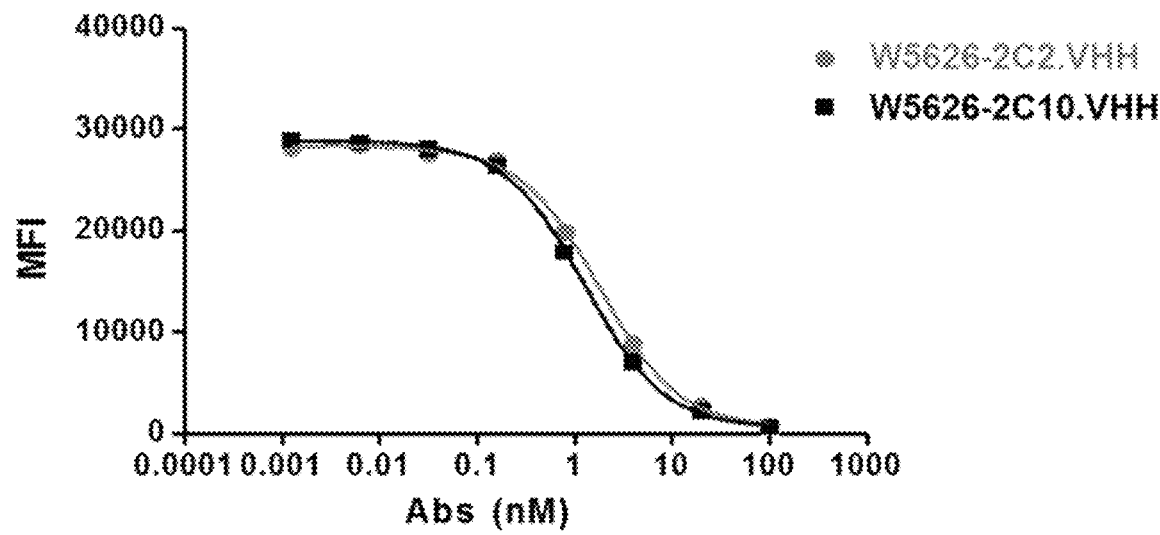
FIG. 5B shows the epitope binning test of W5626-2C10.VHH and W5626-2C2. VHH against each other.
Figure 5B:
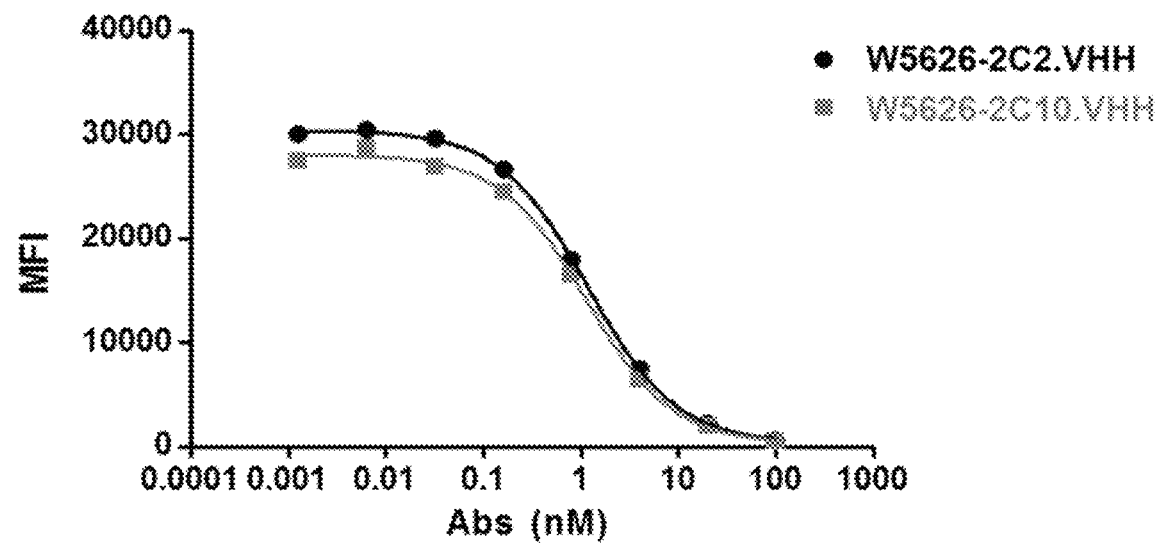

The result show that W5626-2C2.VHH and W5626-2C10.VHH do not share the similar epitope bin with Erbitux or W562-BMK3 (FIG. 5A). W5626-2C2 and W5626-2C10 shared the similar epitope bin with each other (FIG. 5B).

6. Affinity Measured by FACS

Human, cyno, mouse EGFR and human EGFRvIII transfected cells were transferred in to 96-well U-bottom plates (BD) at a density of $5 \times 10^4$ cells/well, respectively. Testing antibodies were 1:3.16-fold serially diluted in 1% BSA-PBS and incubated with the cells at 4° C. for 1 hr. The secondary antibody, Alexa647 conjugated goat anti-human IgG Fc (Jackson Immunoresearch Lab), was added to resuspended cells and incubated at 4° C. in the dark for 1 hr. The cells were then washed once and resuspended in PBS with 1% BSA, and analyzed by flow cytometery (BD). Fluorescence intensity was converted to bound molecules/cell based on the quantitative beads (Quantum™ MESF Kits, Bangs Laboratories). $K_D$ was calculated using Graphpad Prism5. The affinities of W5626-2C2-z22 and W5626-2C10-z5 to cell surface human, cyno, mouse EGFR and human hEGFRIII are shown in Table 4.

TABLE 4

| Affinity | | W5626-2C2-z22 | W5626-2C10-z5 |
|---|---|---|---|
| Human EGFR | Bmax (M) | 8.6E−10 | 9.2E−10 |
| | $k_0$ (M) | 1.1E−09 | 1.4E−09 |
| | $r^2$ | 0.98 | 0.98 |
| Human EGFRvIII | Bmax (M) | 5.3E−10 | 5.9E−10 |
| | $k_0$ (M) | 2.4E−10 | 3.2E−10 |
| | $r^2$ | 0.99 | 0.99 |
| Mouse EGFR | Bmax (M) | 1.0E−09 | 8.9E−10 |
| | $k_0$ (M) | 5.1E−10 | 5.4E−10 |
| | $r^2$ | 0.98 | 1.00 |
| Monkey EGFR | Bmax (M) | 2.3E−10 | 2.3E−10 |
| | $k_0$ (M) | 2.6E−10 | 2.3E−10 |
| | $r^2$ | 0.98 | 1.00 |

7. Surface Plasmon Resonance (SPR)-Based Kinetic Affinity Determination

The binding affinities of W5626-2C2-z22 and W5626-2C10-z5 to human EGFR ECD protein (W562-hPro1.ECD.his) were detected by SPR assay using ProteOn XPR36. Each antibody was captured on an anti-human IgG Fc antibody immobilized GLM sensor chip (Bio-Rad). W562-hPro1.ECD.his at different concentrations was injected over the sensor chip at a flow rate of 100 uL/min for an association phase of 240 s, followed by 1800 s dissociation. The chip was regenerated by 10 mM glycine (pH 1.5) after each binding cycle. The sensorgrams of blank surface and buffer channel were subtracted from the test sensorgrams. The experimental data was fitted by 1:1 binding model using Langmiur analysis. Molecular weight of 85 kDa was used to calculate the molar concentration of analyte. The binding affinities of W5626-2C2-z22 and W5626-2C10-z5 to human EGFR are summarized in Table 5.

TABLE 5

| Analyte | Ligand | ka (1/Ms) | kd (1/s) | $K_D$ (M) |
|---|---|---|---|---|
| Human EGFR | Erbitux | 4.09E+06 | 1.26E−03 | 3.08E−10 |
| | W5626-2C2-z22 | 6.49E+05 | 2.09E−03 | 3.22E−09 |
| | W5626-2C10-z5 | 6.46E+05 | 1.05E−04 | 1.62E−10 |

8. Thermal Stability by DSF Assay

A DSF assay was performed using Real-Time Fluorescent Quantitative PCR (QuantStudio 7 Flex, Thermo Fisher Scientific). Briefly, 19 µL of antibody solution was mixed with 1 µL of 62.5×SYPRO Orange solution (Invitrogen) and added to a 96 well plate (Biosystems). The plate was heated from 26° C. to 95° C. at a rate of 2° C./min, and the resulting fluorescence data were collected. The negative derivatives of the fluorescence changes with respect to different temperatures were calculated, and the maximal value was defined as melting temperature $T_m$. If a protein has multiple unfolding transitions, the first two $T_m$ were reported, named as $T_{m1}$ and $T_{m2}$. $T_{m1}$ is always interpreted as the formal melting temperature $T_m$ to facilitate comparisons between different proteins. Data collection and $T_m$ calculation were conducted automatically by its operation software (QuantStudio Real-Time PCR PCR Software v1.3).

Figure 6:
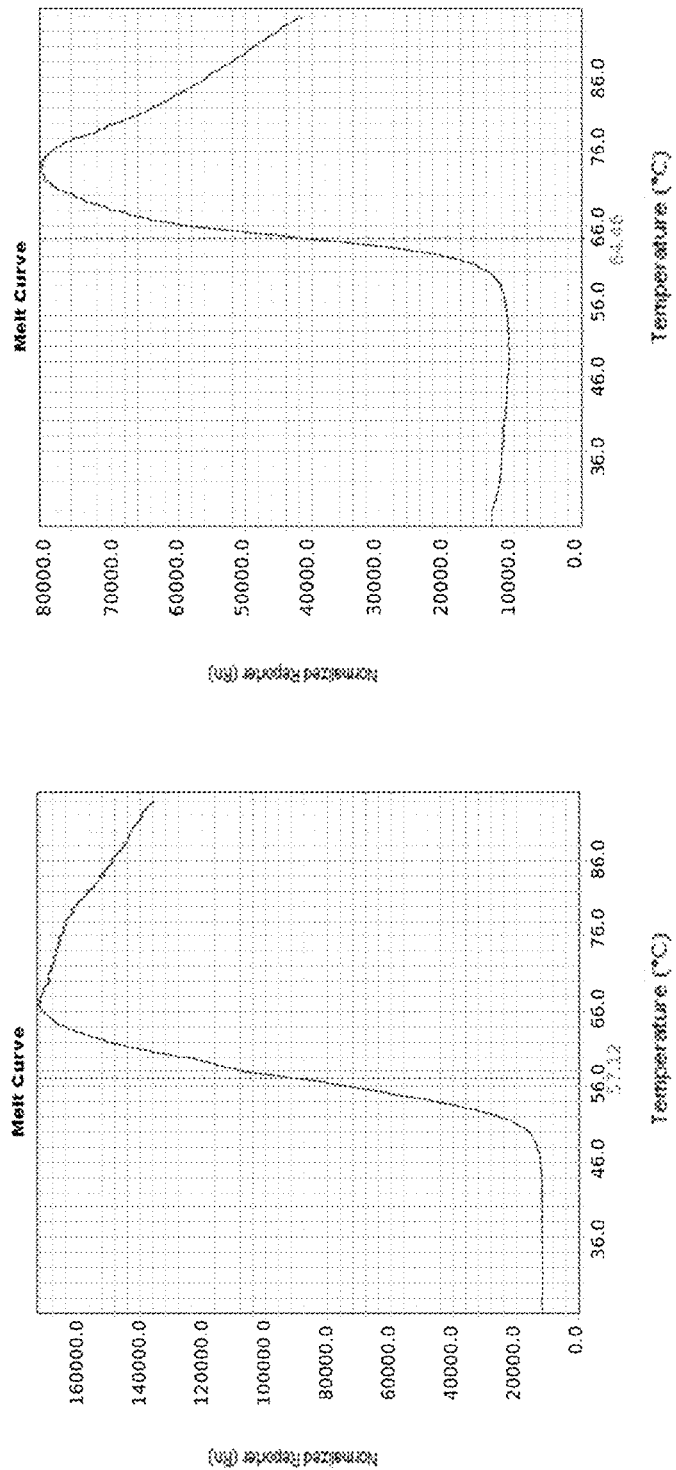
FIG. 6 shows the thermal stability of W5626-2C10-z5 and W5626-2C2-z22 as measured by DSF.

The results show that W5626-2C2-z22 and W5626-2C10-z5 are stable in thermal stability DSF test. The $T_m$ of the two Abs are 57.1 and 64.5° C., respectively (FIG. 6).

9. Serum Stability

Figure 7:
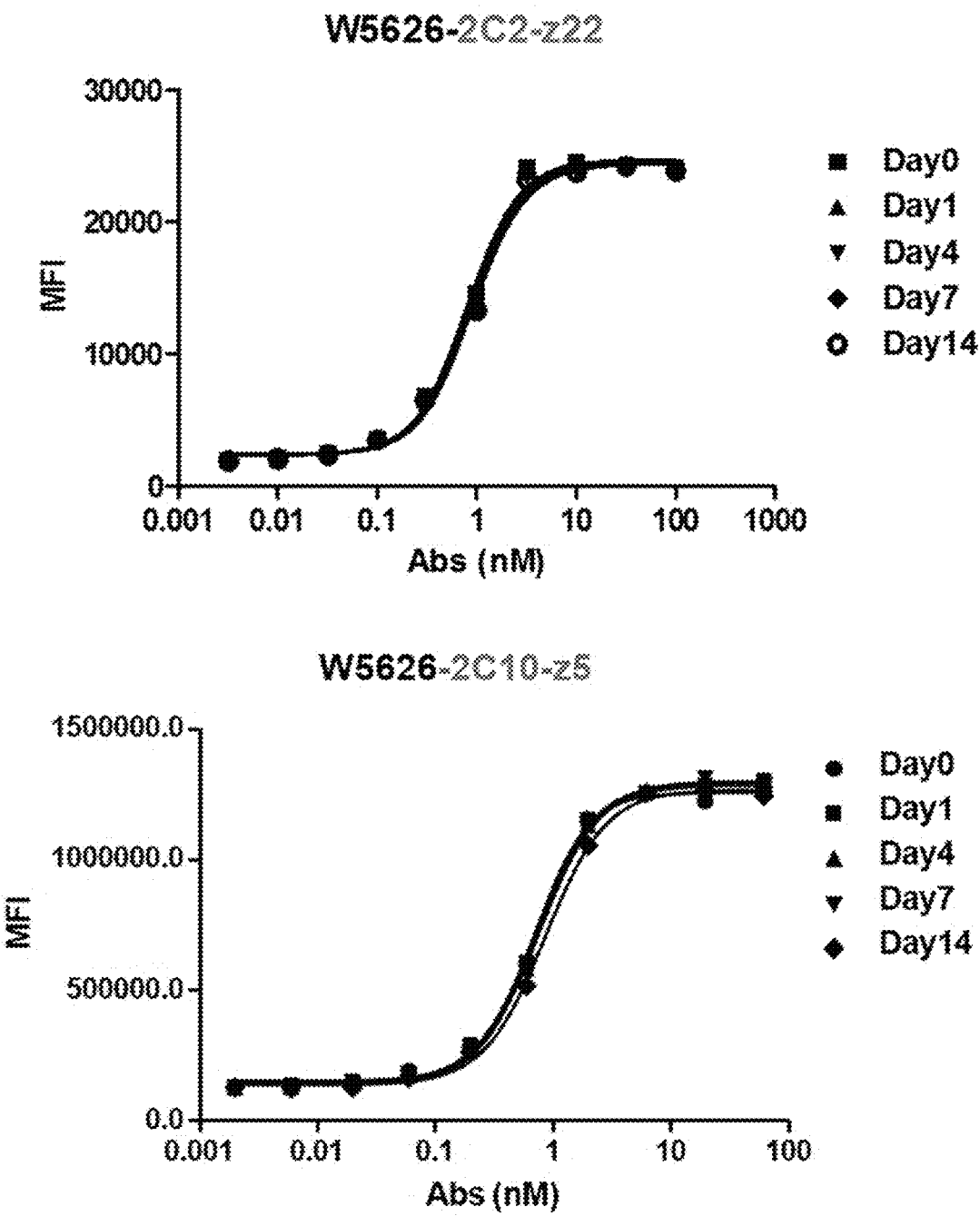
FIG. 7 shows the serum stability of W5626-2C10-z5 and W5626-2C2-z22 for at least 14 days as measured by FACS.

Freshly collected human blood was incubated in polystyrene tubes without anticoagulant for 30 minutes at room temperature. The Serum was collected after centrifugation the blood at 4000 rpm for 10 minutes. Repeat the centrifugation until the serum was clarifying. Gently mix antibodies with serum and ensure the serum content >95%. The mix aliquots were incubated at 37° C. for 0 day, 1 day, 4 days, 7 days and 14 days, respectively. At the indicated time point the samples were quickly-frozen in liquid nitrogen and stored at −80° C. until analysis. The cell bindings of the serial dilutions of the antibody samples to A432 cells were analyzed by FACS. Four-parameter non-linear regression analysis was used to obtain $EC_{50}$ values for cell binding using GraphPad Prism 5 software (GraphPad Software, La Jolla, Calif.). FIG. 7 shows that W5626-2C2-z22 and W5626-2C10-z5 are stable in serum stability test.

10. Non-Specific Binding (ELISA)

Non-specific binding ELISA was performed in 96-well high binding plates (Nunc-Immuno Plate, Thermo Scientific). The plate was coated with various antigens at 2 µg/mL overnight at 4° C. After blocking with 2% BSA-PBS, 10 µg/ml of c-Myc and his-tagged VHH fragments of W5626-2C2-z22 and W5626-2C10-z5 were added to the plate and incubated for 2 hours. The plates were subsequently incubated with the secondary antibody Goat anti-cMyc-HRP (Bethyl) for additional 1 hour. The HRP signal was detected by adding TMB substrate and the reaction was stopped after 12 minutes using 2M HCl. The absorbance at 450 nm was read using a microplate reader (Molecular Device). All incubation steps were performed at room temperature. The plate was washed with PBST (0.05% Tween20-PBS) between each step. No non-specific binding is observed as shown in Table 6.

TABLE 6

| Antigen/Cell Antibodies | Non-specific binding by ELISA OD A450 | | | | | | | |
|---|---|---|---|---|---|---|---|---|
| | Factor Eight | FGFR.his | CD147 | PD-1.his | CTLA4.his | W317-hPro1.ECD.his | CD22.his | VEGF.his |
| W5626-2C2-z22 (VHH) | 0.05 | 0.05 | 0.06 | 0.06 | 0.07 | 0.07 | 0.06 | 0.07 |
| W5626-2C10-z5 (VHH) | 0.04 | 0.05 | 0.04 | 0.04 | 0.04 | 0.05 | 0.05 | 0.05 |
| Ag + Goat anti-cmyc-HRP | 0.04 | 0.05 | 0.04 | 0.05 | 0.04 | 0.06 | 0.04 | 0.06 |

| Antigen/Cell Antibodies | Non-specific binding by ELISA OD A450 | | | | | | |
|---|---|---|---|---|---|---|---|
| | CD3.his | HER3.his | OX40.his | 4-1BB.his | CD40 | HSA | Background (non-coating) |
| W5626-2C2-z22 (VHH) | 0.06 | 0.06 | 0.05 | 0.06 | 0.06 | 0.07 | 0.06 |
| W5626-2C10-z5 (VHH) | 0.04 | 0.04 | 0.04 | 0.05 | 0.05 | 0.05 | 0.05 |
| Ag + Goat anti-cmyc-HRP | 0.04 | 0.05 | 0.04 | 0.06 | 0.05 | 0.06 | 0.05 |

Sequence Listing

The sequence listing submitted herewith in the ASCII text file entitled "SEQUENCE LISTING127501004US1," created Sep. 15, 2020, with a file size of 8,682 bytes, is incorporated herein by reference in its entirety.

What is claimed is:

1. An antibody polypeptide comprising a heavy chain variable domain that specifically binds to EGFR, wherein the heavy chain variable domain comprises:
   a) a heavy chain variable region comprising CDR1 of SEQ ID NO: 1, CDR2 of SEQ ID NO: 2 and CDR3 of SEQ ID NO: 3; or
   b) a heavy chain variable region comprising CDR1 of SEQ ID NO: 4, CDR2 of SEQ ID NO: 5 and CDR3 of SEQ ID NO: 6.

2. The antibody polypeptide of claim 1, wherein the heavy chain variable domain comprises a sequence selected from the group consisting of SEQ ID NO: 7, SEQ ID NO: 9, SEQ ID NO: 11 and SEQ ID NO: 13.

3. The antibody polypeptide of claim 2, further comprising an immunoglobulin constant region, optionally a constant region of human Ig, or optionally a constant region of human IgG1.

4. The antibody polypeptide of claim 1, capable of specifically binding to human EGFR at an $EC_{50}$ value of no more than 1 nM as measured by flow cytometry.

5. The antibody polypeptide of claim 1, capable of specifically binding to human EGFRvIII at an $EC_{50}$ value of no more than 2.5 nM as measured by flow cytometry.

6. The antibody polypeptide of claim 1, capable of specifically binding to Cynomolgus monkey EGFR, and/or mouse EGFR.

7. A pharmaceutical composition comprising the antibody polypeptide of claim 1, and a pharmaceutically acceptable carrier.

* * * * *